(12) United States Patent
Shimizu et al.

(10) Patent No.: US 10,545,418 B2
(45) Date of Patent: Jan. 28, 2020

(54) ELECTROPHOTOGRAPHIC PHOTOSENSITIVE MEMBER, PROCESS CARTRIDGE, AND IMAGE FORMING APPARATUS

(71) Applicant: KYOCERA Document Solutions Inc., Osaka (JP)

(72) Inventors: Tomofumi Shimizu, Osaka (JP); Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 16/092,013

(22) PCT Filed: Mar. 17, 2017

(86) PCT No.: PCT/JP2017/010965
§ 371 (c)(1),
(2) Date: Oct. 8, 2018

(87) PCT Pub. No.: WO2017/187838
PCT Pub. Date: Nov. 2, 2017

(65) Prior Publication Data
US 2019/0086825 A1 Mar. 21, 2019

(30) Foreign Application Priority Data
Apr. 25, 2016 (JP) .................. 2016-087037

(51) Int. Cl.
G03G 5/06 (2006.01)
C07C 211/54 (2006.01)
C07D 241/36 (2006.01)

(52) U.S. Cl.
CPC .......... G03G 5/0638 (2013.01); C07C 211/54 (2013.01); C07D 241/36 (2013.01)

(58) Field of Classification Search
CPC .................................................. G03G 5/0638
See application file for complete search history.

(56) References Cited

U.S. PATENT DOCUMENTS 5,102,757 A * 4/1992 Akasaki ................ C07C 255/34
430/100
5,389,478 A * 2/1995 Yoshida ............... G03G 5/0638
358/296
(Continued)

FOREIGN PATENT DOCUMENTS

CN 105693631 A * 6/2016
JP H10-324682 A 12/1998
(Continued)

OTHER PUBLICATIONS

English language translation of JP 2001-305755 (Nov. 2001).*

*Primary Examiner* — Christopher D Rodee
(74) *Attorney, Agent, or Firm* — Studebaker & Brackett PC

(57) ABSTRACT

An electrophotographic photosensitive member (1) includes a conductive substrate (2) and a photosensitive layer (3). The photosensitive layer (3) is a single-layer photosensitive layer containing at least a charge generating material, an electron transport material, a hole transport material, and a binder resin. The electron transport material includes a naphthoquinone derivative represented by general formula (1). An amount of triboelectric charge of calcium carbonate as measured by charging the calcium carbonate through friction with the photosensitive layer (3) is at least +7 μC/g. In general formula (1), $R^{11}$ and $R^{12}$ are respectively the same as $R^{11}$ and $R^{12}$ described in the description.

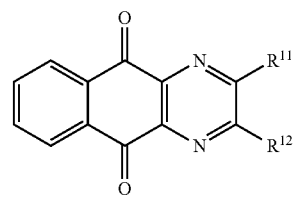

(1)

14 Claims, 4 Drawing Sheets

(56) References Cited

U.S. PATENT DOCUMENTS

| | | | | |
|---|---|---|---|---|
| 5,393,628 A | * | 2/1995 | Ikezue | G03G 5/0521 |
| | | | | 430/58.5 |
| 5,976,742 A | | 11/1999 | Sugai et al. | |
| 2014/0120464 A1 | * | 5/2014 | Iwashita | G03G 15/75 |
| | | | | 430/56 |
| 2018/0299797 A1 | * | 10/2018 | Shimizu | G03G 5/0618 |
| 2018/0356743 A1 | * | 12/2018 | Shimizu | G03G 5/0564 |
| 2018/0356744 A1 | * | 12/2018 | Shimizu | G03G 5/0618 |

FOREIGN PATENT DOCUMENTS

| | | | | |
|---|---|---|---|---|
| JP | 2001305755 A | * | 11/2001 | |
| JP | 2001312075 A | * | 11/2001 | |
| JP | 2005070122 A | * | 3/2005 | |
| JP | 2010151871 A | * | 7/2010 | |
| JP | 2012208231 A | * | 10/2012 | |
| JP | 2017197438 A | * | 11/2017 | |

\* cited by examiner

ELECTROPHOTOGRAPHIC PHOTOSENSITIVE MEMBER, PROCESS CARTRIDGE, AND IMAGE FORMING APPARATUS

TECHNICAL FIELD

The present invention relates to an electrophotographic photosensitive member, a process cartridge, and an image forming apparatus.

BACKGROUND ART

An electrophotographic photosensitive member is used in an electrophotographic image forming apparatus. A single-layer electrophotographic photosensitive member or a multi-layer electrophotographic photosensitive member is for example used as the electrophotographic photosensitive member. The electrophotographic photosensitive member includes a photosensitive layer. The single-layer electrophotographic photosensitive member includes a single-layer photosensitive layer having a charge generation function and a charge transport function. The multi-layer electrophotographic photosensitive member includes a photosensitive layer that includes a charge generating layer having the charge generation function and a charge transport layer having the charge transport function.

An image defect so-called a white spot phenomenon may occur in image formation using an electrophotographic image forming apparatus. The white spot phenomenon is for example a phenomenon in which a minute image defect (more specifically, a circular image defect having a diameter of at least 0.5 mm and no greater than 2.5 mm) occurs in a region (image region) formed by transfer of a toner image onto a recording medium.

A photosensitive layer included in a traditional electrophotographic photosensitive member contains for example a compound represented by chemical formula (E-1) shown below (hereinafter may be referred to as a compound (E-1)) or a compound represented by chemical formula (E-2) shown below (hereinafter may be referred to as a compound (E-2)).

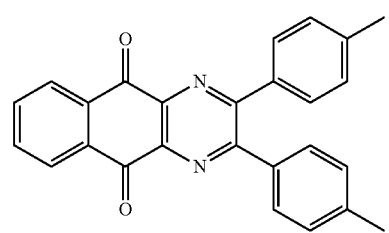

(E-1)

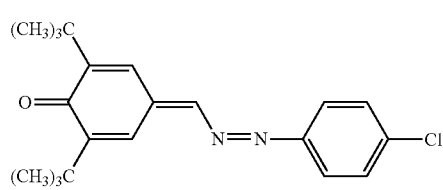

(E-2)

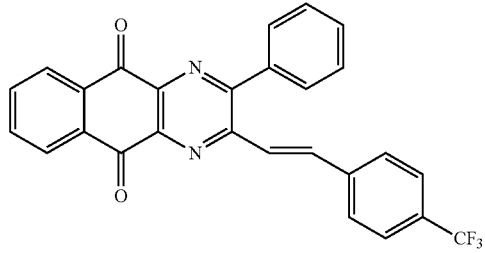

(E-3)

Also, a photosensitive layer included in an electrophotographic photosensitive member disclosed in Patent Literature 1 contains for example a compound represented by chemical formula (E-3) shown below (hereinafter may be referred to as a compound (E-3)).

CITATION LIST

Patent Literature

[Patent Literature 1]
Japanese Patent Application Laid-Open Publication No. H10-324682

SUMMARY OF INVENTION

Technical Problem

However, the above-described traditional electrophotographic photosensitive member and the electrophotographic photosensitive member disclosed in Patent Literature 1 could not sufficiently inhibit occurrence of the white spot phenomenon.

The present invention was made in view of the foregoing and has its object of providing an electrophotographic photosensitive member that inhibits occurrence of the white spot phenomenon. Other objects of the present invention are to provide a process cartridge that inhibits occurrence of the white spot phenomenon and to provide an image forming apparatus that inhibits occurrence of the white spot phenomenon.

Solution to Problem

An electrophotographic photosensitive member of the present invention includes a conductive substrate and a photosensitive layer. The photosensitive layer is a single-layer photosensitive layer containing at least a charge generating material, an electron transport material, a hole transport material, and a binder resin. The electron transport material includes a naphthoquinone derivative represented by general formula (1). An amount of triboelectric charge of calcium carbonate as measured by charging the calcium carbonate through friction with the photosensitive layer is at least +7 µC/g.

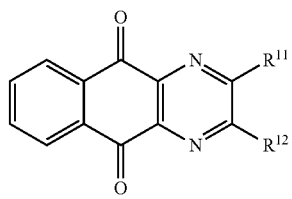

(1)

In general formula (1), $R^{11}$ and $R^{12}$ each represent, independently of each other, a chemical group selected from the group consisting of: an alkyl group having a carbon number of at least 1 and no greater than 8; an aryl group having a carbon number of at least 6 and no greater than 14 and optionally having a substituent; an aralkyl group having a carbon number of at least 7 and no greater than 20 and optionally having a substituent; and a cycloalkyl group having a carbon number of at least 3 and no greater than 10 and optionally having a substituent. At least one of the chemical groups respectively represented by $R^{11}$ and $R^{12}$ is substituted with one or more halogen atoms.

A process cartridge of the present invention includes the above-described electrophotographic photosensitive member.

An image forming apparatus of the present invention includes an image bearing member, a charger, a light exposure device, a developing device, and a transfer device. The image bearing member is the above-described electrophotographic photosensitive member. The charger positively charges a surface of the image bearing member. The light exposure device irradiates the charged surface of the image bearing member with light to form an electrostatic latent image on the surface of the image bearing member. The developing device develops the electrostatic latent image into a toner image. The transfer device transfers the toner image from the surface of the image bearing member to a recording medium while in contact with the surface of the image bearing member.

Advantageous Effects of Invention

The electrophotographic photosensitive member of the present invention can inhibit occurrence of the white spot phenomenon. Also, the process cartridge and the image forming apparatus of the present invention can inhibit occurrence of the white spot phenomenon.

DESCRIPTION OF EMBODIMENTS

Figure 1A:
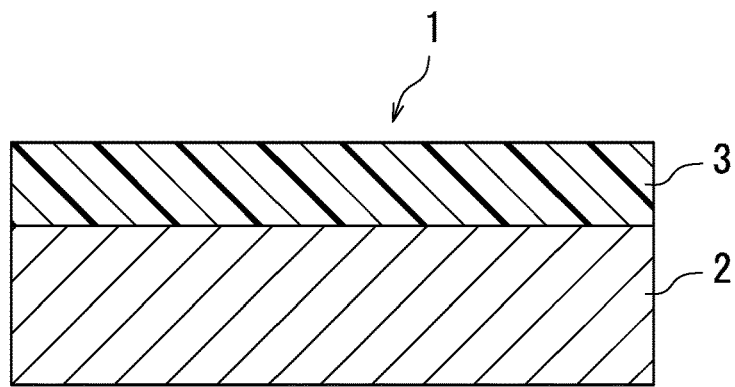
FIG. 1A is a schematic cross-sectional view illustrating an example of an electrophotographic photosensitive member according to the first embodiment of the present invention.

The following describes embodiments of the present invention in detail. The present invention is by no means limited to the following embodiments. The present invention can be practiced with alterations appropriately made within a scope of the objects of the present invention. Note that although some overlapping explanations may be omitted as appropriate, such omission does not limit the gist of the present invention.

In the following description, the term "-based" may be appended to the name of a chemical compound in order to form a generic name encompassing both the chemical compound itself and derivatives thereof. When the term "-based" is appended to the name of a chemical compound used in the name of a polymer, the term indicates that a repeating unit of the polymer originates from the chemical compound or a derivative thereof.

In the following description, a halogen atom, an alkyl group having a carbon number of at least 1 and no greater than 8, an alkyl group having a carbon number of at least 1 and no greater than 6, an alkyl group having a carbon number of at least 1 and no greater than 4, an alkyl group having a carbon number of at least 1 and no greater than 3, an alkoxy group having a carbon number of at least 1 and no greater than 6, an aryl group having a carbon number of at least 6 and no greater than 14, an aryl group having a carbon number of at least 6 and no greater than 10, an aralkyl group having a carbon number of at least 7 and no greater than 20, an aralkyl group having a carbon number of at least 7 and no greater than 14, a cycloalkyl group having a carbon number of at least 3 and no greater than 10, a cycloalkyl group having a carbon number of at least 5 and no greater than 7, a cycloalkylidene group having a carbon number of at least 3 and no greater than 10, and a cycloalkylidene group having a carbon number of at least 5 and no greater than 7 refer to the followings unless otherwise stated.

Examples of halogen atoms (halogen groups) include fluorine atom (fluoro group), chlorine atom (chloro group), bromine atom (bromo group), and iodine atom (iodine group).

The alkyl group having a carbon number of at least 1 and no greater than 8 is an unsubstituted straight chain or branched chain alkyl group. Examples of alkyl groups having a carbon number of at least 1 and no greater than 8 include methyl group, ethyl group, n-propyl group, isopropyl group, n-butyl group, s-butyl group, t-butyl group, pentyl group, isopentyl group, neopentyl group, n-hexyl group, n-heptyl group, and n-octyl group.

The alkyl group having a carbon number of at least 1 and no greater than 6 is an unsubstituted straight chain or branched chain alkyl group. Examples of alkyl groups having a carbon number of at least 1 and no greater than 6 include methyl group, ethyl group, n-propyl group, isopropyl group, n-butyl group, s-butyl group, t-butyl group, pentyl group, isopentyl group, neopentyl group, and hexyl group.

The alkyl group having a carbon number of at least 1 and no greater than 4 is an unsubstituted straight chain or branched chain alkyl group. Examples of alkyl groups having a carbon number of at least 1 and no greater than 4 include methyl group, ethyl group, n-propyl group, isopropyl group, n-butyl group, s-butyl group, and t-butyl group.

The alkyl group having a carbon number of at least 1 and no greater than 3 is an unsubstituted straight chain or branched chain alkyl group. Examples of alkyl groups having a carbon number of at least 1 and no greater than 3 include methyl group, ethyl group, n-propyl group, and isopropyl group.

The alkoxy group having a carbon number of at least 1 and no greater than 6 is an unsubstituted alkoxy group. Examples of alkoxy groups having a carbon number of at least 1 and no greater than 6 include methoxy group, ethoxy group, n-propoxy group, isopropoxy group, n-butoxy group, s-butoxy group, t-butoxy group, pentoxy group, and hexyloxy group.

The aryl group having a carbon number of at least 6 and no greater than 14 is an unsubstituted aryl group. Examples of aryl groups having a carbon number of at least 6 and no greater than 14 include unsubstituted monocyclic aromatic hydrocarbon groups having a carbon number of at least 6 and no greater than 14, unsubstituted condensed bicyclic aromatic hydrocarbon groups having a carbon number of at least 6 and no greater than 14, and unsubstituted condensed tricyclic aromatic hydrocarbon groups having a carbon number of at least 6 and no greater than 14. Examples of aryl groups having a carbon number of at least 6 and no greater than 14 include phenyl group, naphthyl group, anthryl group, and phenanthryl group.

The aryl group having a carbon number of at least 6 and no greater than 10 is an unsubstituted aryl group. Examples of aryl groups having a carbon number of at least 6 and no greater than 10 include unsubstituted monocyclic aromatic hydrocarbon groups having a carbon number of at least 6 and no greater than 10, unsubstituted condensed bicyclic aromatic hydrocarbon groups having a carbon number of at least 6 and no greater than 10, and unsubstituted condensed tricyclic aromatic hydrocarbon groups having a carbon number of at least 6 and no greater than 10. Examples of aryl groups having a carbon number of at least 6 and no greater than 10 include phenyl group and naphthyl group.

The aralkyl group having a carbon number of at least 7 and no greater than 20 is an unsubstituted aralkyl group. Examples of aralkyl groups having a carbon number of at least 7 and no greater than 20 include phenylmethyl group, phenylethyl group, phenylpropyl group, phenylbutyl group, phenylpentyl group, phenylhexyl group, 1-naphthylmethyl group, 2-naphthylmethyl group, 9-anthracenemethyl group, and 9-phenanthrylmethyl group The aralkyl group having a carbon number of at least 7 and no greater than 14 is an unsubstituted aralkyl group. Examples of aralkyl groups having a carbon number of at least 7 and no greater than 14 include phenylmethyl group, phenylethyl group, phenylpropyl group, phenylbutyl group, phenylpentyl group, phenylhexyl group, 1-naphthylmethyl group, and 2-naphthylmethyl group.

The cycloalkyl group having a carbon number of at least 3 and no greater than 10 is an unsubstituted cycloalkyl group. Examples of cycloalkyl groups having a carbon number of at least 3 and no greater than 10 include cyclopropyl group, cyclobutyl group, cyclopentyl group, cyclohexyl group, cycloheptyl group, cyclooctyl group, cyclononyl group, and cyclodecyl group.

The cycloalkyl group having a carbon number of at least 5 and no greater than 7 is an unsubstituted cycloalkyl group. Examples of cycloalkyl groups having a carbon number of at least 5 and no greater than 7 include cyclopentyl group, cyclohexyl group, and cycloheptyl group.

The cycloalkylidene group having a carbon number of at least 3 and no greater than 10 is an unsubstituted cycloalkylidene group. Examples of cycloalkylidene groups having a carbon number of at least 3 and no greater than 10 include cyclopropylidene group, cyclobutylidene group, cyclopentylidene group, cyclohexylidene group, cycloheptylidene group, cyclooctylidene group, cyclononylidene group, and cyclodecylidene group.

The cycloalkylidene group having a carbon number of at least 5 and no greater than 7 is an unsubstituted cycloalkylidene group. Examples of cycloalkylidene groups having a carbon number of at least 5 and no greater than 7 include cyclopentylidene group, cyclohexylidene group, and cycloheptylidene group.

First Embodiment: Electrophotographic Photosensitive Member

Figure 1B:
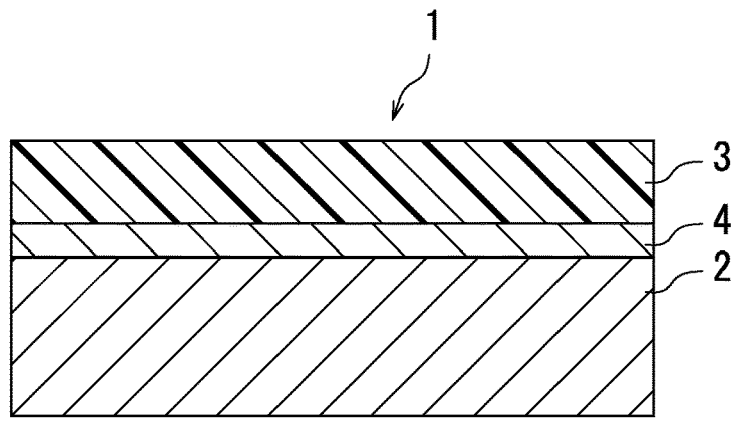
FIG. 1B is a schematic cross-sectional view illustrating an example of the electrophotographic photosensitive member according to the first embodiment of the present invention.
Figure 1C:
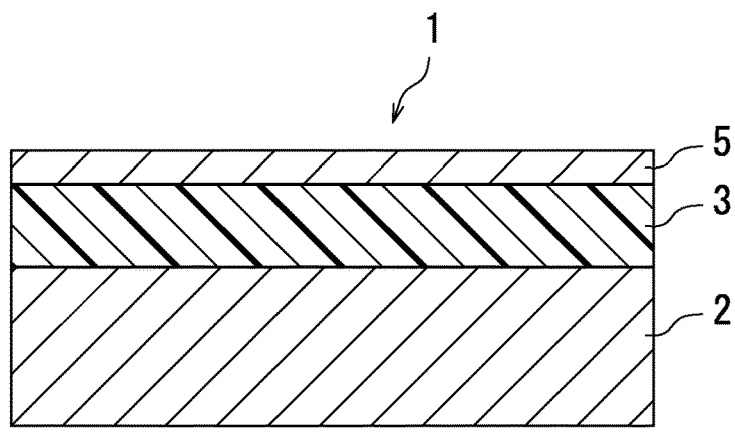
FIG. 1C is a schematic cross-sectional view illustrating an example of the electrophotographic photosensitive member according to the first embodiment of the present invention.

The first embodiment of the present invention relates to an electrophotographic photosensitive member. The following describes structure of the electrophotographic photosensitive member (hereinafter may be referred to as a photosensitive member) with reference to FIGS. 1A to 1C. FIGS. 1A to 1C each illustrate an example of a photosensitive member 1 according to the first embodiment.

As illustrated in FIG. 1A, the photosensitive member 1 includes for example a conductive substrate 2 and a photosensitive layer 3. The photosensitive layer 3 is located directly or indirectly on the conductive substrate 2. The photosensitive layer 3 may for example be located directly on the conductive substrate 2 as illustrated in FIG. 1A. The photosensitive member 1 may further include an intermediate layer. As illustrated in FIG. 1B, an intermediate layer 4 may be provided between the conductive substrate 2 and the photosensitive layer 3. Also, as illustrated in FIGS. 1A and 1B, the photosensitive layer 3 may be exposed as an outermost layer. The photosensitive member 1 may further include a protective layer. As illustrated in FIG. 1C, a protective layer 5 may be provided on the photosensitive layer 3.

The photosensitive layer is a single-layer photosensitive layer containing at least a charge generating material, an electron transport material, a hole transport material, and a binder resin. The electron transport material includes a naphthoquinone derivative represented by general formula (1) (hereinafter may be referred to as a naphthoquinone derivative (1)). An amount of triboelectric charge of calcium carbonate as measured by charging the calcium carbonate through friction with the photosensitive layer is at least +7 μC/g. The photosensitive member according to the first embodiment can inhibit occurrence of a white spot phenomenon. Reasons for this are inferred as follows.

Here, the white spot phenomenon will be described to facilitate description. An electrophotographic image forming apparatus includes an image bearing member (photosensitive member), a charger, a light exposure device, a developing device, and a transfer device. In a case of an image forming apparatus adopting a direct transfer process, the transfer device transfers a toner image developed by the developing device to a recording medium (for example, recording paper). More specifically, the transfer device transfers the toner image developed on a surface of the photosensitive member to the recording medium. As a result, the toner image is formed on the recording medium.

In the transfer of the toner image, the recording medium may be rubbed against the surface of the photosensitive member and the recording medium may be charged (so-called triboelectric charging). In such a case, the recording medium tends to be charged to the same polarity as the charging polarity (positive polarity) of the photosensitive member and chargeability of the recording medium tends to decrease. Alternatively, the recording medium tends to be charged to the opposite polarity (negative polarity) (i.e., oppositely charged). When the recording medium is charged as described above, minute components of the recording medium (for example, paper dust) may move to the surface of the photosensitive member to be attached thereto. When the minute components are attached to an image region on the surface of the photosensitive member, an image formed on the recording medium may have a defect (white spot). A phenomenon in which such an image defect occurs is called white spot phenomenon. A method for evaluating occurrence of the white spot phenomenon will be described in detail in Examples.

The photosensitive member according to the first embodiment includes the photosensitive layer containing the naphthoquinone derivative (1). The naphthoquinone derivative (1) includes a halogen atom. An amount of triboelectric charge of calcium carbonate as measured by charging the calcium carbonate through friction with the photosensitive layer is at least +7 µC/g. Therefore, even when the recording medium is rubbed against the surface of the photosensitive member according to the first embodiment in the transfer device, chargeability of the recording medium, which is the same polarity as the charging polarity of the photosensitive member, tends not to decrease. Also, the recording medium tends not to be charged to the opposite polarity. It is thought that as a result, minute components (for example, paper dust) tend not to be attached to the surface of the photosensitive member, and occurrence of the white spot phenomenon is inhibited.

A method for measuring the amount of triboelectric charge of calcium carbonate will be described in detail in Examples. The amount of triboelectric charge of calcium carbonate is at least +7 µC/g, and preferably at least +7 µC/g and no greater than +15 µC/g. Calcium carbonate is a main component of paper dust. When the amount of triboelectric charge of calcium carbonate is smaller than +7 µC/g, repelling force acting between the photosensitive member and paper dust is not sufficiently large. Therefore, paper dust tends to be attached to the surface of the photosensitive member to cause occurrence of the white spot phenomenon.

The thickness of the photosensitive layer is not particularly limited so long as the photosensitive layer can sufficiently serves as the photosensitive layer. The thickness of the photosensitive layer is preferably at least 5 µm and no greater than 100 µm, and more preferably at least 10 µm and no greater than 50 µm.

The photosensitive layer may further contain additives. The following describes the conductive substrate, the charge generating material, the electron transport material, the hole transport material, the binder resin, the additives, and the intermediate layer as elements of the photosensitive member. Also, a method for producing the photosensitive member will be described.

[1. Conductive Substrate]

The conductive substrate is not particularly limited so long as the conductive substrate can be used in the photosensitive member. It is only required that at least a surface portion of the conductive substrate be formed from an electrically conductive material. An example of the conductive substrate is a conductive substrate formed from an electrically conductive material. Another example of the conductive substrate is a conductive substrate coated with an electrically conductive material. Examples of electrically conductive materials include aluminum, iron, copper, tin, platinum, silver, vanadium, molybdenum, chromium, cadmium, titanium, nickel, palladium, and indium. One of the above-listed electrically conductive materials may be used independently, or two or more of the above-listed electrically conductive materials may be used in combination. Examples of combinations of two or more electrically conductive materials include alloys (specific examples include aluminum alloys, stainless steel, and brass). Among the above-listed electrically conductive materials, aluminum or an aluminum alloy is preferable in terms of favorable charge mobility from the photosensitive layer to the conductive substrate.

The shape of the conductive substrate is appropriately selected according to the structure of an image forming apparatus. Examples of the shape of the conductive substrate include a sheet-like shape and a drum-like shape. Also, the thickness of the conductive substrate is appropriately selected according to the shape of the conductive substrate.

[2. Charge Generating Material]

The charge generating material is not particularly limited so long as the charge generating material can be used in the photosensitive member. Examples of charge generating materials include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (specific examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. One charge generating material may be used independently, or two or more charge generating materials may be used in combination.

Examples of phthalocyanine-based pigments include a metal-free phthalocyanine represented by chemical formula (C-1) (hereinafter referred to as a compound (C-1)) or metal phthalocyanines. Examples of metal phthalocyanines include a titanyl phthalocyanine represented by chemical formula (C-2) (hereinafter may be referred to as a compound (C-2)), hydroxygallium phthalocyanines, and chlorogallium phthalocyanines. Phthalocyanine-based pigments may be crystalline or noncrystalline. No specific limitation is placed on the crystal form (specific examples include X-form, α-form, β-form, Y-form, V-form, and II-form) of phthalocyanine-based pigments. Phthalocyanine-based pigments having various crystal forms can be used.

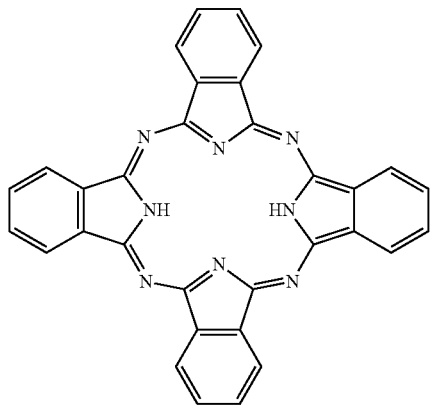

(C-1)

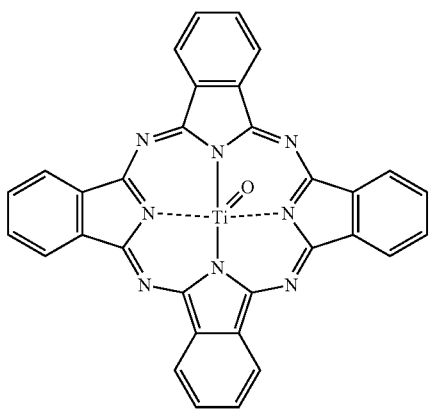

(C-2)

Examples of crystalline metal-free phthalocyanines include a metal-free phthalocyanine having X-form crystal structure (hereinafter may be referred to as an X-form metal-free phthalocyanine). Examples of crystalline titanyl phthalocyanines include titanyl phthalocyanines respectively having α-form, β-form, and Y-form crystal structures (hereinafter may be referred to as an α-form titanyl phthalocyanine, a β-form titanyl phthalocyanine, and a Y-form titanyl phthalocyanine, respectively). Examples of crystalline hydroxygallium phthalocyanines include a hydroxygallium phthalocyanine having V-form crystal structure. Examples of crystalline chlorogallium phthalocyanines include a chlorogallium phthalocyanine having II-form crystal structure.

A photosensitive member having sensitivity within a wavelength range of 700 nm or greater is preferably used for example in an image forming apparatus adopting a digital optical system. Examples of image forming apparatuses adopting the digital optical system include a laser beam printer and a facsimile machine including a light source such as a semiconductor laser. Phthalocyanine-based pigments are preferable as the charge generating material in terms of their high quantum yield in the wavelength range of 700 nm or greater, and metal-free phthalocyanines are more preferable. In the photosensitive member including the photosensitive layer that contains the naphthoquinone derivative (1), the charge generating material preferably includes the X-form metal-free phthalocyanine in order to more effectively inhibit occurrence of the white spot phenomenon.

The Y-form titanyl phthalocyanine has a main peak for example at a Bragg angle (2θ±0.2°) of 27.2° on a CuKα characteristic X-ray diffraction spectrum. The main peak on the CuKα characteristic X-ray diffraction spectrum is a peak having the largest or second largest intensity in a Bragg angle (2θ±0.2°) range of from 3° to 40°.

Anthanthrone-based pigments are preferably used as the charge generating material in photosensitive members adopted in image forming apparatuses including a short-wavelength laser light source. The wavelength of short-wavelength laser light is for example at least 350 nm and no greater than 550 nm.

The amount of the charge generating material is preferably at least 0.1 parts by mass and no greater than 50 parts by mass relative to 100 parts by mass of the binder resin contained in the photosensitive layer, and more preferably at least 0.5 parts by mass and no greater than 30 parts by mass.

[3. Electron Transport Material]

The electron transport material includes the naphthoquinone derivative (1). The naphthoquinone derivative (1) is represented by general formula (1).

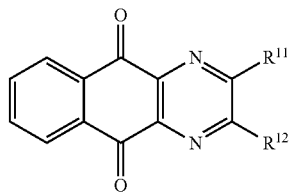

(1)

In general formula (1), $R^{11}$ and $R^{12}$ each represent, independently of each other, a chemical group selected from the group consisting of: an alkyl group having a carbon number of at least 1 and no greater than 8; an aryl group having a carbon number of at least 6 and no greater than 14 and optionally having a substituent; an aralkyl group having a carbon number of at least 7 and no greater than 20 and optionally having a substituent; and a cycloalkyl group having a carbon number of at least 3 and no greater than 10 and optionally having a substituent. At least one of the chemical groups respectively represented by $R^{11}$ and $R^{12}$ is substituted with one or more halogen atoms.

In general formula (1), the alkyl group having a carbon number of at least 1 and no greater than 8 and represented by $R^{11}$ or $R^{12}$ is preferably an alkyl group having a carbon number of at least 1 and no greater than 4, and more preferably a methyl group or an isobutyl group. The alkyl group having a carbon number of at least 1 and no greater than 8 may be substituted with one or more halogen atoms. Examples of alkyl groups having a carbon number of at least 1 and no greater than 8 and substituted with one or more halogen atoms include a chloromethyl group.

In general formula (1), the aryl group having a carbon number of at least 6 and no greater than 14, optionally having a substituent, and represented by $R^{11}$ or $R^{12}$ is preferably an aryl group having a carbon number of at least 6 and no greater than 10 and optionally having a substituent, and more preferably a phenyl group optionally having a substituent. The aryl group having a carbon number of at least 6 and no greater than 14 and optionally having a substituent may be substituted with one or more halogen atoms. The substituent included in the aryl group having a carbon number of at least 6 and no greater than 14 is preferably an alkyl group having a carbon number of at least 1 and no greater than 6, more preferably an alkyl group having a carbon number of at least 1 and no greater than 3, and further preferably a methyl group. The aryl group having a carbon number of at least 6 and no greater than 14 and having an alkyl group having a carbon number of at least 1 and no greater than 6 is preferably a 4-methylphenyl group.

In general formula (1), the aralkyl group having a carbon number of at least 7 and no greater than 20, optionally having a substituent, and represented by $R^{11}$ or $R^{12}$ is preferably an aralkyl group having a carbon number of at least 7 and no greater than 14 and optionally having a substituent. The aralkyl group having a carbon number of at least 7 and no greater than 20 and optionally having a substituent may be substituted with one or more halogen atoms. The substituent included in the aralkyl group having a carbon number of at least 7 and no greater than 20 is preferably an alkyl group having a carbon number of at least 1 and no greater than 6.

In general formula (1), the cycloalkyl group having a carbon number of at least 3 and no greater than 10, optionally having a substituent, and represented by $R^{11}$ or $R^{12}$ is preferably a cycloalkyl group having a carbon number of at least 5 and no greater than 7 and optionally having a substituent. The cycloalkyl group having a carbon number of at least 3 and no greater than 10 and optionally having a substituent may be substituted with one or more halogen atoms. The substituent included in the cycloalkyl group having a carbon number of at least 3 and no greater than 10 is preferably an alkyl group having a carbon number of at least 1 and no greater than 6.

In general formula (1), a total number of halogen atoms included in the chemical groups respectively represented by $R^{11}$ and $R^{12}$ (chemical groups selected from the group consisting of: the alkyl group having a carbon number of at least 1 and no greater than 8; the aryl group having a carbon number of at least 6 and no greater than 14 and optionally having a substituent; the aralkyl group having a carbon number of at least 7 and no greater than 20 and optionally having a substituent; and the cycloalkyl group having a carbon number of at least 3 and no greater than 10 and optionally having a substituent) is preferably at least 1 and no greater than 3, and more preferably 1 or 2. In a configuration in which the total number of the halogen atoms included in the chemical groups respectively represented by $R^{11}$ and $R^{12}$ is at least 1 and no greater than 3, the naphthoquinone derivative (1) has a stronger effect of inhibiting occurrence of the white spot phenomenon. The halogen atoms included in the chemical groups respectively represented by $R^{11}$ and $R^{12}$ are each preferably a chlorine atom or a fluorine atom.

Preferably, $R^{11}$ and $R^{12}$ in general formula (1) differ from each other. A naphthoquinone derivative (1) in which $R^{11}$ and $R^{12}$ differ from each other, that is, a naphthoquinone derivative (1) in an asymmetric structure is highly soluble in a solvent. Therefore, use of such a naphthoquinone derivative (1) facilitates preparation of an application liquid for formation of the photosensitive layer of the photosensitive member.

Preferably, either one of $R^{11}$ and $R^{12}$ in general formula (1) represents: an alkyl group having a carbon number of at least 1 and no greater than 3 and substituted with one or more halogen atoms; or a phenyl group substituted with one or more halogen atoms. In the above configuration, the other of $R^{11}$ and $R^{12}$ preferably represents: a phenyl group optionally having an alkyl group having a carbon number of at least 1 and no greater than 3; or an alkyl group having a carbon number of at least 1 and no greater than 4. The halogen atoms are each preferably a chlorine atom or a fluorine atom.

In general formula (1), either one of $R^{11}$ and $R^{12}$ preferably represents a phenyl group substituted with one or more halogen atoms and the other of $R^{11}$ and $R^{12}$ preferably represents an alkyl group having a carbon number of at least 1 and no greater than 4. In a configuration in which either one of $R^{11}$ and $R^{12}$ represents a phenyl group substituted with one or more halogen atoms and the other of $R^{11}$ and $R^{12}$ represents an alkyl group having a carbon number of at least 1 and no greater than 4, the naphthoquinone derivative (1) has a stronger effect of inhibiting occurrence of the white spot phenomenon. When either one of $R^{11}$ and $R^{12}$ represents a phenyl group substituted with one or more halogen atoms, the phenyl group is substituted with the halogen atom(s) at at least one of an ortho position (o-position), a meta position (m-position), and a para position (p-position), and preferably at the meta position. Examples of phenyl groups substituted with one or more halogen atoms include a 4-chlorophenyl group, a 4-fluorophenyl group, and a 3,5-dichlorophenyl group. Among these, the 3,5-dichlorophenyl group is particularly preferable.

Specific examples of the naphthoquinone derivative (1) include naphthoquinone derivatives represented by chemical formulas (1-1), (1-2), (1-3), (1-4), and (1-5), respectively (hereinafter may be referred to as naphthoquinone derivatives (1-1), (1-2), (1-3), (1-4), and (1-5), respectively).

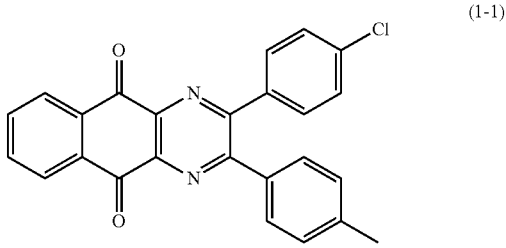

(1-1)

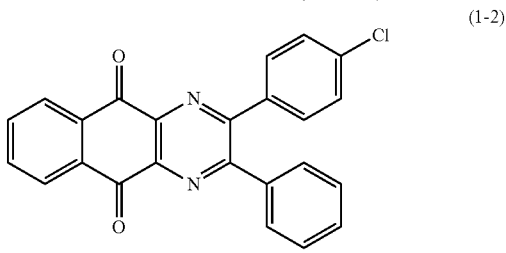

(1-2)

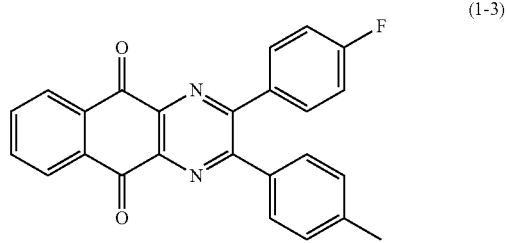

(1-3)

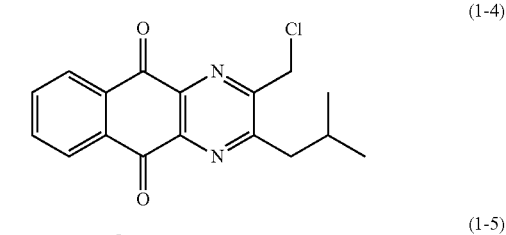

(1-4)

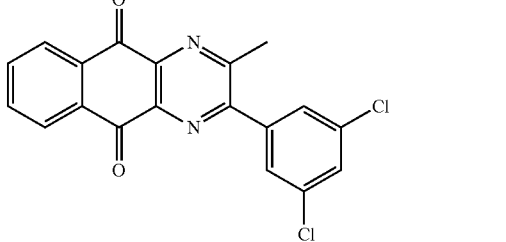

(1-5)

Among the naphthoquinone derivatives (1-1) to (1-5), a naphthoquinone derivative represented by general formula (1) in which either one of $R^{11}$ and $R^{12}$ represents a phenyl group substituted with one or more halogen atoms and the other of $R^{11}$ and $R^{12}$ represents an alkyl group having a carbon number of at least 1 and no greater than 4, that is, the naphthoquinone derivative (1-5) is preferable in terms of having a stronger effect of inhibiting occurrence of the white spot phenomenon as described above. Reasons for this are inferred as follows. That is, the naphthoquinone derivative (1-5) includes two halogen atoms (halogen substituents) having high electronegativity. Accordingly, the naphthoquinone derivative (1-5) has a stronger effect of positively charging paper dust than compounds having the structures of the naphthoquinone derivatives (1-1) to (1-4) when coming into contact with paper dust.

(Method for Producing Naphthoquinone Derivative (1))

The naphthoquinone derivative (1) is produced for example by a reaction represented by reaction formula (R-1) (hereinafter may be referred to as a reaction (R-1)) and a reaction represented by reaction formula (R-2) (hereinafter may be referred to as a reaction (R-2)), or a method conforming therewith. A method for producing the naphthoquinone derivative (1) includes for example the reaction (R-1) and the reaction (R-2).

none (a1). By contrast, when the potassium phthalimide (a2) is added in an amount of no greater than 4 mol relative to 1 mol of the dihalogenonaphthoquinone (a1), unreacted potassium phthalimide (a2) tends not to be left after the reaction (R-1), and therefore, the diaminonaphthoquinone (A) can be easily purified.

In the reaction (R-1), the dihalogenonaphthoquinone (a1) and the potassium phthalimide (a2) in the solvent are refluxed under stirring at a reflux temperature that is preferably at least 50° C. and no higher than 100° C. for a reflux period that is preferably at least 2 hours and no longer than 8 hours. Examples of the solvent include acetonitrile, N,N-dimethylformamide (DMF), tetrahydrofuran, and dimethyl sulfoxide.

After the reflux under stirring in the reaction (R-1), heating under stirring in the presence of hydrazine ($NH_2NH_2$) is carried out at a heating temperature that is preferably at least 50° C. and no higher than 100° C. for a heating period that is preferably at least 0.5 hours and no longer than 2 hours.

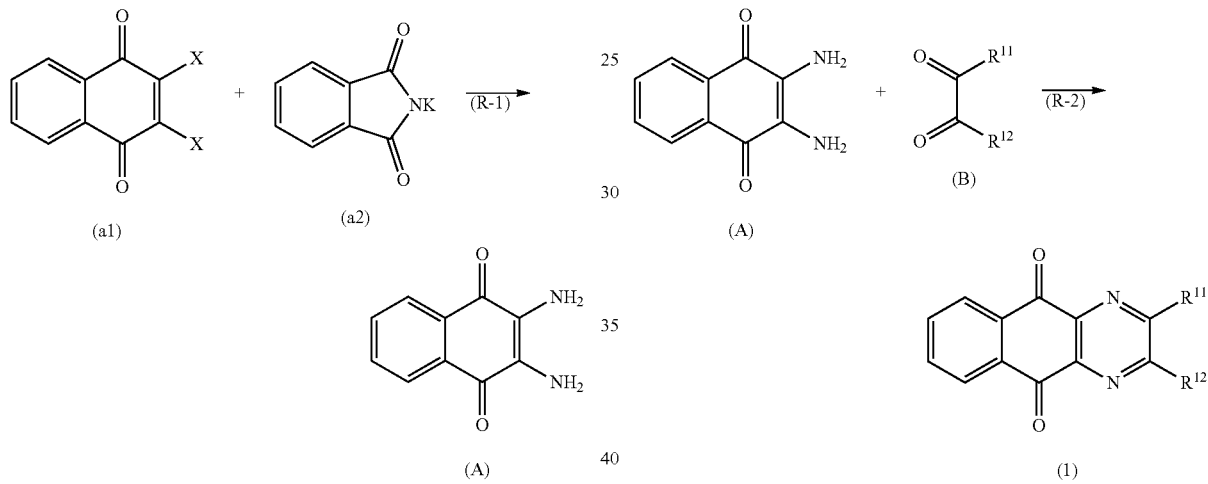

In the reaction (R-1), 1 equivalent of a compound represented by general formula (a1) (2,3-dihalogeno-1,4-naphthoquinone, hereinafter may be referred to as dihalogeno naphthoquinone (a1)) and 2 equivalents of a compound represented by chemical formula (a2) (potassium phthalimide, hereinafter may be referred to as potassium phthalimide (a2)) are heated in a solvent to cause reflux under stirring. Then, the reaction system is left to stand to cool to room temperature (approximately 25° C.), whereby a reaction intermediate product is obtained. Subsequently, the reaction intermediate product is heated under stirring in the presence of hydrazine ($NH_2NH_2$) to cause a reaction (hydrazinolysis). Through the above, 1 equivalent of a compound represented by chemical formula (A) (2,3-diamino-1,4-naphthoquinone, hereinafter may be referred to as diaminonaphthoquinone (A)) is yielded.

In general formula (a1), X represents a halogen atom (halogen group). The halogen atom (halogen group) represented by X is preferably a chlorine atom (chloro group).

In the reaction (R-1), at least 2 mol and no greater than 4 mol of the potassium phthalimide (a2) is preferably added relative to 1 mol of the dihalogenonaphthoquinone (a1). The yield of the diaminonaphthoquinone (A) can be easily increased by adding at least 2 mol of the potassium phthalimide (a2) relative to 1 mol of the dihalogenonaphthoqui- In the reaction (R-2), 1 equivalent of the diaminonaphthoquinone (A) and 1 equivalent of a compound represented by general formula (B) (a diketone derivative, hereinafter may be referred to as a diketone derivative (B)) are heated in a solvent in the presence of an acid catalyst to cause reflux under stirring. Then, the solvent is evaporated from the reaction system. Through the above, 1 equivalent of the naphthoquinone derivative (1) is yielded.

In general formula (B), $R^{11}$ and $R^{12}$ are the same as $R^{11}$ and $R^{12}$ in general formula (1), respectively.

The reaction (R-2) includes an addition reaction of the diaminonaphthoquinone (A) to the diketone derivative (B) and a subsequent dehydration reaction. Accordingly, it is preferable to add substantially 1 mol equivalent of the diketone derivative (B) relative to 1 mol of the diaminonaphthoquinone (A).

In the reaction (R-2), the diaminonaphthoquinone (A) and the diketone derivative (B) in the solvent are refluxed under stirring at a reflux temperature that is preferably at least 50° C. and no higher than 100° C. for a reflux period that is preferably at least 2 hours and no longer than 6 hours. Examples of the solvent include methanol, ethanol, isopropanol, and butanol. Examples of the acid catalyst include acetic acid, concentrated sulfuric acid, and p-toluenesulfonic acid. The amount of the acid catalyst is preferably at least 0.2 mol and no greater than 0.8 mol relative to 1 mol of the diaminonaphthoquinone (A). The acid catalyst may function as the solvent.

Production of the naphthoquinone derivative (1) may include another process as necessary (for example, a solvent evaporation process or a purification process). The solvent evaporation process may be performed for example by a known method (a specific example is solvent evaporation under a reduced pressure). The purification process may be performed for example by a known method (specific examples include filtration, chromatography, and crystallization).

In addition to the naphthoquinone derivative (1), an additional electron transport material other than the naphthoquinone derivative (1) may be further included in the electron transport material. The additional electron transport material is appropriately selected from known electron transport materials.

Examples of the additional electron transport material include quinone-based compounds (quinone-based compounds other than the naphthoquinone derivative (1)), diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of the quinone-based compounds include diphenoquinone-based compounds, azoquinone-based compounds, anthraquinone-based compounds, nitroanthraquinone-based compounds, and dinitroanthraquinone-based compounds. One of the above-listed electron transport materials may be used independently, or two or more of the above-listed electron transport materials may be used in combination.

The amount of the electron transport material(s) is preferably at least 5 parts by mass and no greater than 100 parts by mass relative to 100 parts by mass of the binder resin contained in the photosensitive layer, and more preferably at least 10 parts by mass and no greater than 80 parts by mass.

The amount of the naphthoquinone derivative (1) in the electron transport material(s) is preferably at least 80% by mass relative to a total mass of the electron transport material(s), more preferably at least 90% by mass, and particularly preferably 100% by mass.

[4. Hole Transport Material]

A nitrogen-containing cyclic compound or a condensed polycyclic compound can for example be used as the hole transport material. Examples of nitrogen-containing cyclic compounds and condensed polycyclic compounds include diamine derivatives (specific examples include benzidine derivatives, N,N,N',N'-tetraphenylphenylenediamine derivatives, N,N,N',N'-tetraphenylnaphtylenediamine derivatives, and N,N,N',N'-tetraphenylphenanthrylenediamine derivatives), oxadiazole-based compounds (specific examples include 2,5-di(4-methylaminophenyl)-1,3,4-oxadiazole), styryl compounds (specific examples include 9-(4-diethylaminostyryl)anthracene), carbazole compounds (specific examples include polyvinyl carbazole), organic polysilane compounds, pyrazoline-based compounds (specific examples include 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. One of the above-listed hole transport materials may be used independently, or two or more of the above-listed hole transport materials may be used in combination. Among the above-listed hole transport materials, a compound represented by general formula (2) (a benzidine derivative) is preferable.

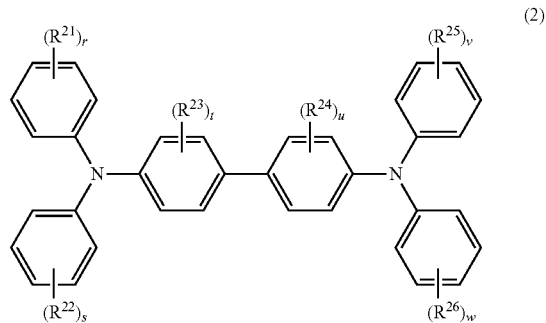

In general formula (2), $R^{21}$, $R^{22}$, $R^{23}$, $R^{24}$, $R^{25}$, and $R^{26}$ each represent, independently of one another, an alkyl group having a carbon number of at least 1 and no greater than 6 or an alkoxy group having a carbon number of at least 1 and no greater than 6. Also, r, s, v, and w each represent, independently of one another, an integer of at least 0 and no greater than 5. Further, t and u each represent, independently of one another, an integer of at least 0 and no greater than 4.

In general formula (2), $R^{21}$ to $R^{26}$ each represent, independently of one another, preferably an alkyl group having a carbon number of at least 1 and no greater than 6, more preferably an alkyl group having a carbon number of at least 1 and no greater than 3, and further preferably a methyl group. Preferably, r, s, v, and w each represent, independently of one another, 0 or 1. Preferably, t and u each represent 0.

Among compounds represented by general formula (2), a compound represented by chemical formula (H-1) (hereinafter may be referred to as a compound (H-1)) is preferable.

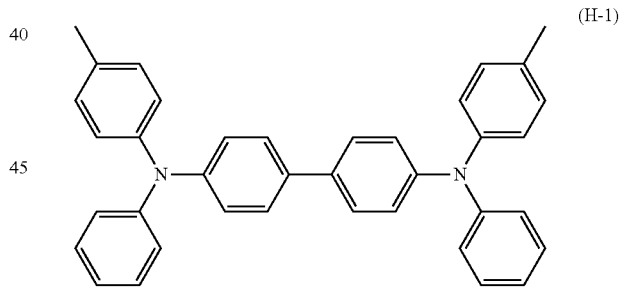

The amount of the hole transport material is preferably at least 10 parts by mass and no greater than 200 parts by mass relative to 100 parts by mass of the binder resin contained in the photosensitive layer, and more preferably at least 10 parts by mass and no greater than 100 parts by mass.

[5. Binder Resin]

The binder resin disperses and secures the charge generating material and the like in the photosensitive layer. Examples of binder resins include thermoplastic resins, thermosetting resins, and photocurable resins. Examples of thermoplastic resins include polycarbonate resins, polyarylate resins, styrene-butadiene resins, styrene-acrylonitrile resins, styrene-maleic acid resins, acrylic acid-based resins, styrene-acrylic acid resins, polyethylene resins, ethylene-vinyl acetate resins, chlorinated polyethylene resins, polyvinyl chloride resins, polypropylene resins, ionomer resins, vinyl chloride-vinyl acetate resins, alkyd resins, polyamide resins, urethane resins, polysulfone resins, diallyl phthalate resins, ketone resins, polyvinyl butyral resins, polyester resins, and polyether resins. Examples of thermosetting resins include silicone resins, epoxy resins, phenolic resins, urea resins, and melamine resins. Examples of photocurable resins include epoxy-acrylic acid-based resins (specific examples include acrylic acid derivative adducts of epoxy compounds) and urethane-acrylic acid-based resins (specific examples include acrylic acid derivative adducts of urethane compounds). One of the above-listed binder resins may be used independently, or two or more of the above-listed binder resins may be used in combination.

Among the above-listed resins, a polycarbonate resin is preferable since use of a polycarbonate resin enables production of a photosensitive layer that is excellent in balance between processability, mechanical strength, optical properties, and abrasion resistance. Examples of preferable polycarbonate resins include a polycarbonate resin represented by general formula (3) (hereinafter may be referred to as a polycarbonate resin (3)).

The binder resin preferably has a viscosity average molecular weight of at least 40,000, and more preferably at least 40,000 and no greater than 52,500. In a configuration in which the binder resin has a viscosity average molecular weight of at least 40,000, abrasion resistance of the photosensitive member can be easily improved. In a configuration in which the binder resin has a viscosity average molecular weight of no greater than 52,500, the binder resin readily dissolves in a solvent in formation of the photosensitive layer. Accordingly, viscosity of an application liquid for photosensitive layer formation does not become excessively high. The above facilitates formation of the photosensitive layer.

[6. Additives]

The photosensitive layer may contain various additives so long as the additives do not have an adverse influence on electrophotographic characteristics of the photosensitive member. Examples of additives include antidegradants (spe-

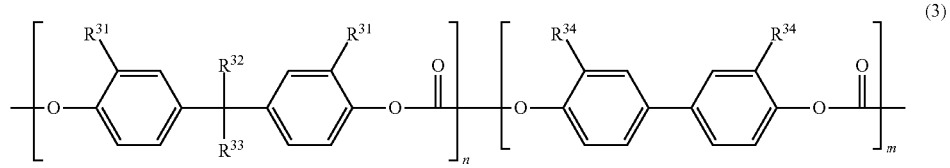

(3)

In general formula (3), $R^{31}$, $R^{32}$, $R^{33}$, and $R^{34}$ each represent, independently of one another, a hydrogen atom or an alkyl group having a carbon number of at least 1 and no greater than 6. $R^{32}$ and $R^{33}$ may be bonded to each other to form a cycloalkylidene group having a carbon number of at least 3 and no greater than 10. In general formula (3), n and m each represent an integer of at least 0 and satisfy the following equation: n+m=100. Further, n represents an integer of at least 60 and no greater than 100.

In general formula (3), $R^{31}$ and $R^{34}$ each preferably represent a hydrogen atom. $R^{32}$ and $R^{33}$ are preferably bonded to each other to form a cycloalkylidene group having a carbon number of at least 3 and no greater than 10, more preferably bonded to each other to form a cycloalkylidene group having a carbon number of at least 5 and no greater than 7, and particularly preferably bonded to each other to form a cyclohexylidene group.

Examples of the polycarbonate resin (3) include polycarbonate resins represented by chemical formulas (R-1) and (R-2) (hereinafter may be referred to as polycarbonate resins (R-1) and (R-2), respectively).

cific examples include antioxidants, radical scavengers, quenchers, and ultraviolet absorbing agents), softeners, surface modifiers, extenders, thickeners, dispersion stabilizers, waxes, acceptors, donors, surfactants, plasticizers, sensitizers, and leveling agents. Examples of the antioxidants include hindered phenol, hindered amine, paraphenylenediamine, arylalkane, hydroquinone, spirochromane, spiroindanone, derivatives of the aforementioned compounds, organosulfur compounds, and organophosphorus compounds.

[7. Intermediate Layer]

The intermediate layer contains for example inorganic particles and a resin for intermediate layer use (an intermediate layer resin). In the presence of the intermediate layer, an electric current generated when the photosensitive member is irradiated with light flows smoothly while insulation is maintained to such an extent that a leakage current can be prevented. Therefore, an increase in resistance can be easily inhibited by the presence of the intermediate layer.

Examples of the inorganic particles include particles of metals (specific examples include aluminum, iron, and cop-

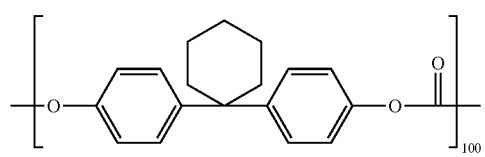

(R-1)

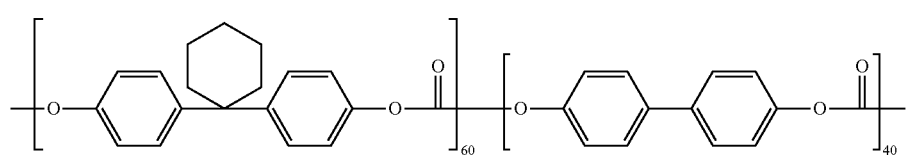

(R-2)

per), particles of metal oxides (specific examples include titanium oxide, alumina, zirconium oxide, tin oxide, and zinc oxide), and particles of non-metal oxides (specific examples include silica). One type of the above-listed inorganic particles may be used independently, or two or more types of the above-listed inorganic particles may be used in combination.

The intermediate layer resin is not particularly limited so long as the intermediate layer resin can be used for formation of the intermediate layer.

The intermediate layer may contain various additives so long as the additives do not have an adverse influence on electrophotographic characteristics of the photosensitive member. The intermediate layer may contain additives similar to the additives that may be contained in the photosensitive layer.

[8. Method for Producing Photosensitive Member]

The following describes an example of methods for producing the photosensitive member 1 with reference to FIG. 1A. The method for producing the photosensitive member 1 for example includes formation of the photosensitive layer. In formation of the photosensitive layer, an application liquid for photosensitive layer formation is applied onto the conductive substrate 2, and a solvent contained in the application liquid for photosensitive layer formation is removed to form the photosensitive layer 3. The application liquid for photosensitive layer formation includes at least a charge generating material, the naphthoquinone derivative (1) as an electron transport material, a hole transport material, a binder resin, and the solvent. The application liquid for photosensitive layer formation is prepared by dissolving or dispersing the charge generating material, the naphthoquinone derivative (1) as the electron transport material, the hole transport material, and the binder resin in the solvent. An additive may be added to the application liquid for photosensitive layer formation, as necessary.

The solvent contained in the application liquid for photosensitive layer formation is not particularly limited so long as components contained in the application liquid for photosensitive layer formation can be dissolved or dispersed in the solvent. Examples of the solvent include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, and diethylene glycol dimethyl ether), ketones (specific examples include acetone, methyl ethyl ketone, and cyclohexanone), esters (specific examples include ethyl acetate and methyl acetate), dimethyl formaldehyde, N,N-dimethylformamide (DMF), and dimethyl sulfoxide. One of the above-listed solvents may be used independently, or two or more of the above-listed solvents may be used in combination. Among the above-listed solvents, a solvent other than the halogenated hydrocarbons is preferable in order to improve workability in the production of the photosensitive member 1.

The application liquid for photosensitive layer formation is prepared by mixing the respective components and dispersing the components in the solvent. Mixing or dispersion may be performed using for example a bead mill, a roll mill, a ball mill, an attritor, a paint shaker, or an ultrasonic disperser.

In order to improve dispersibility of the respective components or improve surface smoothness of the photosensitive layer 3 to be formed, the application liquid for photosensitive layer formation may contain for example a surfactant or a leveling agent.

The method for applying the application liquid for photosensitive layer formation is not particularly limited so long as the application liquid for photosensitive layer formation can be uniformly applied onto the conductive substrate 2, for example. Examples of the method for applying include dip coating, spray coating, spin coating, and bar coating.

The method for removing the solvent contained in the application liquid for photosensitive layer formation is not particularly limited so long as the solvent can be evaporated from the application liquid for photosensitive layer formation. Examples of the method for removing the solvent include heating, depressurization, and a combination of heating and depressurization. Specific examples of the method for removing the solvent include thermal treatment (hot-air drying) using a high-temperature dryer or a reduced-pressure dryer. The thermal treatment is preferably carried out for example at a temperature of at least 40° C. and no higher than 150° C. for a period of at least 3 minutes and no longer than 120 minutes.

Note that the method for producing the photosensitive member 1 may further include either or both of formation of the intermediate layer 4 and formation of the protective layer 5, as necessary. In formation of the intermediate layer 4 and formation of the protective layer 5, methods appropriately selected from known methods are adopted.

The photosensitive member 1 is for example used as an image bearing member in an image forming apparatus.

Through the above, the photosensitive member according to the first embodiment has been described. The photosensitive member according to the first embodiment can inhibit occurrence of the white spot phenomenon.

Second Embodiment: Image Forming Apparatus

The second embodiment of the present invention relates to an image forming apparatus. The image forming apparatus according to the second embodiment includes an image bearing member, a charger, a light exposure device, a developing device, and a transfer device. The charger positively charges a surface of the image bearing member. The light exposure device irradiates the charged surface of the image bearing member with light to form an electrostatic latent image on the surface of the image bearing member. The developing device develops the electrostatic latent image into a toner image. The transfer device transfers the toner image from the surface of the image bearing member to a recording medium while in contact with the surface of the image bearing member. The image bearing member is the photosensitive member according to the first embodiment.

The image forming apparatus according to the second embodiment can inhibit occurrence of the white spot phenomenon. Reasons for this are inferred as follows. In the image forming apparatus according to the second embodiment adopting the direct transfer process, when the image bearing member and the recording medium come into contact with each other in the transfer device, the recording medium tends to be positively charged through friction. The surface of the image bearing member is positively charged by the charger. Accordingly, electrostatic repelling force acts between the surface of the image bearing member and the triboelectrically charged recording medium. It is thought as a result, minute components (for example, paper dust) derived from the recording medium (for example, paper) are hardly attached to the surface of the image bearing member, resulting in inhibition of occurrence of the white spot phenomenon.

Figure 2:
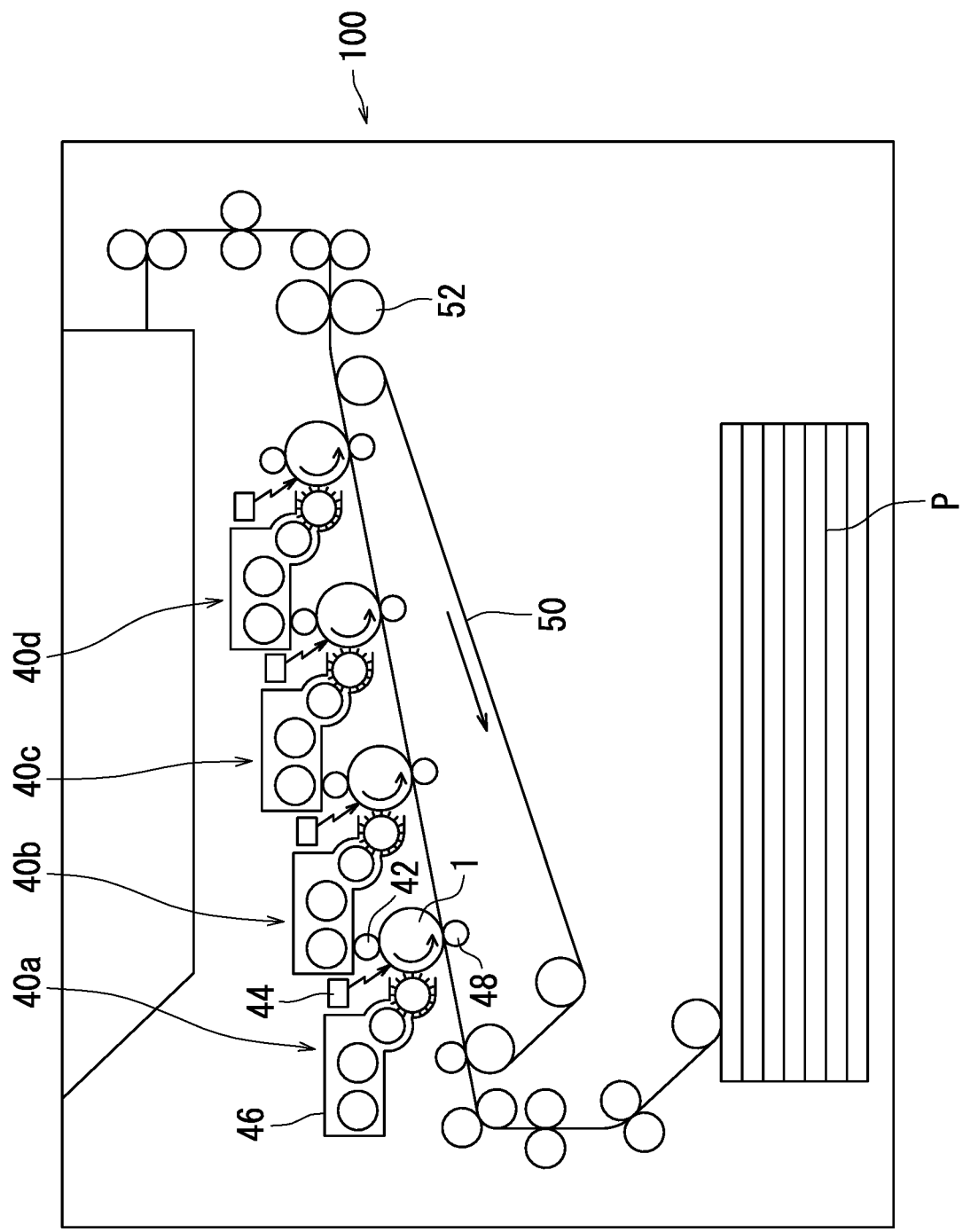
FIG. 2 is a diagram illustrating an example of an image forming apparatus according to the second embodiment of the present invention.

The following describes an image forming apparatus 100 with reference to FIG. 2. FIG. 2 illustrates an example of a configuration of the image forming apparatus 100.

The image forming apparatus 100 is not particularly limited so long as the image forming apparatus 100 is an electrophotographic image forming apparatus. The image forming apparatus 100 may for example be a monochrome image forming apparatus or a color image forming apparatus. In a case where the image forming apparatus 100 is a color image forming apparatus, the image forming apparatus 100 adopts a tandem system, for example. The following describes the image forming apparatus 100 adopting the tandem system as an example.

The image forming apparatus 100 includes image formation units 40a, 40b, 40c, and 40d, a transfer belt 50, and a fixing device 52. In the following description, each of the image formation units 40a, 40b, 40c, and 40d may be referred to as an image formation unit 40 when there is no need to distinguish the respective image formation units.

The image formation unit 40 includes an image bearing member 1, a charger 42, a light exposure device 44, a developing device 46, and a transfer device 48. The image bearing member 1 is located at a center position of the image formation unit 40. The image bearing member 1 is rotatable in an arrowed direction (counter-clockwise direction). The charger 42, the light exposure device 44, the developing device 46, and the transfer device 48 are arranged around the image bearing member 1 in this order starting from the charger 42 as a reference from the upstream in the rotation direction of the image bearing member 1. Note that the image formation unit 40 may further include either or both of a cleaning device (not illustrated) or a static eliminator (not illustrated).

The charger 42 positively charges a surface of the image bearing member 1. The charger 42 is a charger adopting a non-contact charging process or a contact charging process. Examples of the charger 42 adopting the non-contact charging process include a corotron charger and a scorotron charger. Examples of the charger 42 adopting the contact charging process include a charging roller and a charging brush.

The image forming apparatus 100 can include a charging roller as the charger 42. The charging roller charges the surface of the image bearing member 1 while in contact with the surface of the image bearing member 1. In a situation in which minute components are attached to the surface of the image bearing member 1, the minute components are pressed against the surface of the image bearing member 1 by the charging roller in contact with the surface of the image bearing member 1. As a result, the minute components tend to adhere to the surface of the image bearing member 1. However, the image forming apparatus 100 includes the image bearing member 1 that can inhibit occurrence of the white spot phenomenon, which would otherwise be caused by attachment of the minute components derived from a recording medium P. Therefore, even in a configuration in which the image forming apparatus 100 includes the charging roller as the charger 42, minute components hardly adhere to the surface of the image bearing member 1, resulting in inhibition of occurrence of the white spot phenomenon.

The light exposure device 44 irradiates the charged surface of the image bearing member 1 with light. Through the above, an electrostatic latent image is formed on the surface of the image bearing member 1. The electrostatic latent image is formed on the basis of image data input to the image forming apparatus 100.

The developing device 46 develops the electrostatic latent image into a toner image by supplying toner to the surface of the image bearing member 1.

The developing device 46 is capable of cleaning the surface of the image bearing member 1. That is, the image forming apparatus 100 can adopt a so-called blade cleaner-less process. The developing device 46 is capable of removing components remaining on the surface of the image bearing member 1 (hereinafter may be referred to as residual components). An example of the residual components is a toner component, and a more specific example is toner or a detached external additive. Another example of the residual components is a non-toner component (minute component), and a more specific example is paper dust. In the image forming apparatus 100 adopting the blade cleaner-less process, the residual components are not scraped off from the surface of the image bearing member 1 by a cleaner (for example, a cleaning blade). Therefore, in the image forming apparatus 100 adopting the blade cleaner-less process, the residual components usually tend to remain on the surface of the image bearing member 1. However, the image bearing member 1 can inhibit occurrence of the white spot phenomenon, which would otherwise be caused by attachment of minute components derived from the recording medium P. Therefore, even in a configuration in which the blade cleaner-less process is adopted in the image forming apparatus 100 including such an image bearing member 1, minute components, particularly paper dust, hardly remain on the surface of the image bearing member 1. As a result, the image forming apparatus 100 can inhibit occurrence of the white spot phenomenon.

In order that the developing device 46 efficiently cleans the surface of the image bearing member 1, it is preferable that the following conditions (a) and (b) are satisfied.

Condition (a): A contact development process is adopted and peripheral speed (rotational speed) is different between the image bearing member 1 and the developing device 46.

Condition (b): A surface potential of the image bearing member 1 and an electric potential of a development bias satisfy the following expressions (b-1) and (b-2).

$$0\ (V) < \text{electric potential (V) of development bias} < \text{surface potential (V) of non-irradiated region of image bearing member 1 that has not been irradiated with light} \quad \text{(b-1)}$$

$$\text{electric potential (V) of development bias} > \text{surface potential (V) of irradiated region of image bearing member 1 that has been irradiated with light} > 0\ (V) \quad \text{(b-2)}$$

When the contact development process is adopted and there is a difference in peripheral speed between the image bearing member 1 and the developing device 46 as described in condition (a), the surface of the image bearing member 1 comes into contact with the developing device 46, and components attached to the surface of the image bearing member 1 are removed through friction with the developing device 46. The peripheral speed of the developing device 46 is preferably higher than that of the image bearing member 1.

The condition (b) is to be satisfied in a situation in which the charging polarity of toner, the surface potential of the non-irradiated region of the image bearing member 1, the surface potential of the irradiated region of the image bearing member 1, and the electric potential of the development bias are all positive. That is, in the condition (b), it is assumed that a reversal development process is adopted as the development process. Note that the surface potentials of the non-irradiated region and the irradiated region of the image bearing member 1 are measured after the toner image is transferred from the image bearing member 1 to the recording medium P by the transfer device 48 and before the charger 42 charges the surface of the image bearing member 1 in the next turn of the image bearing member 1.

When the expression (b-1) in the condition (b) is satisfied, electrostatic repelling force acting between toner remaining on the image bearing member 1 (hereinafter may be referred to as residual toner) and the non-irradiated region of the image bearing member 1 is larger than electrostatic repelling force acting between the residual toner and the developing device 46. Therefore, residual toner on the non-irradiated region of the image bearing member 1 moves from the surface of the image bearing member 1 to the developing device 46 to be collected.

When the expression (b-2) in the condition (b) is satisfied, electrostatic repelling force acting between the residual toner and the irradiated region of the image bearing member 1 is smaller than the electrostatic repelling force acting between the residual toner and the developing device 46. Therefore, residual toner on the irradiated region of the image bearing member 1 is held on the surface of the image bearing member 1. The toner held on the irradiated region of the image bearing member 1 is directly used for image formation.

The transfer belt 50 conveys the recording medium P to a site between the image bearing member 1 and the transfer device 48. The transfer belt 50 is an endless belt. The transfer belt 50 is capable of circulating in an arrowed direction (clockwise direction).

The transfer device 48 transfers the toner image developed by the developing device 46 from the surface of the image bearing member 1 to the recording medium P. In the transfer of the toner image from the image bearing member 1 to the recording medium P, the image bearing member 1 is in contact with the recording medium P. That is, the image forming apparatus 100 adopts a so-called direct transfer process. The transfer device 48 is a transfer roller, for example.

The image formation units 40a to 40d superimpose toner images in a plurality of colors (for example, four colors of black, cyan, magenta, and yellow) on one another in order on the recording medium P placed on the transfer belt 50. Note that in a case where the image forming apparatus 100 is a monochrome image forming apparatus, the image forming apparatus 100 includes the image formation unit 40a, and the image formation units 40b to 40d are omitted.

The fixing device 52 applies either or both of heat and pressure to the unfixed toner image transferred to the recording medium P by the transfer device 48. The fixing device 52 includes for example either or both of a heating roller and a pressure roller. Through application of either or both of heat and pressure to the toner image, the toner image is fixed to the recording medium P. As a result, an image is formed on the recording medium P.

Through the above, the image forming apparatus according to the second embodiment has been described. The image forming apparatus according to the second embodiment includes the photosensitive member according to the first embodiment as the image bearing member. Therefore, the image forming apparatus according to the second embodiment can inhibit occurrence of the white spot phenomenon.

Third Embodiment: Process Cartridge

The third embodiment of the present invention relates to a process cartridge. The process cartridge according to the third embodiment includes the photosensitive member according to the first embodiment.

The following describes the process cartridge according to the third embodiment with reference to FIG. 2. The process cartridge includes a unitized image bearing member 1. The process cartridge has a configuration in which at least one device selected from the group consisting of the charger 42, the light exposure device 44, the developing device 46, and the transfer device 48 is unitized with the image bearing member 1. The process cartridge is for example equivalent to each of the image formation units 40a to 40d. The process cartridge may further include either or both of a cleaner (not illustrated) and a static eliminator (not illustrated). The process cartridge is designed to be attachable to and detachable from the image forming apparatus 100. Therefore, the process cartridge including the image bearing member 1 is easy to handle and can be replaced easily and rapidly when sensitivity characteristics or the like of the image bearing member 1 degrade.

Through the above, the process cartridge according to the third embodiment has been described. The process cartridge according to the third embodiment includes the photosensitive member according to the first embodiment as the image bearing member. Therefore, the process cartridge according to the third embodiment can inhibit occurrence of the white spot phenomenon.

EXAMPLES

The following more specifically describes the present invention using examples. However, the present invention is by no means limited to the scope of the examples.

<1. Materials of Photosensitive Member>

The following electron transport materials, hole transport material, charge generating material, and binder resins were prepared as materials for forming photosensitive layers of photosensitive members.

[1-1. Electron Transport Material]

Naphthoquinone derivatives (1-1) to (1-5) were prepared as electron transport materials. The naphthoquinone derivatives (1-1) to (1-5) were produced by the following respective methods.

[1-1-1. Production of Naphthoquinone Derivative (1-1)]

The naphthoquinone derivative (1-1) was produced through reactions represented by reaction formula (r-1) and reaction formula (r-2) (hereinafter may be referred to as a reaction (r-1) and a reaction (r-2), respectively).

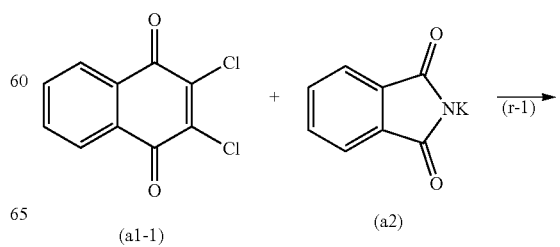

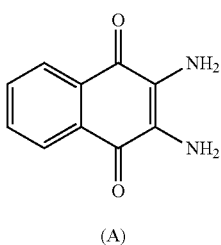

(A)

In the reaction (r-1), 2,3-dichloro-1,4-naphthoquinone represented by chemical formula (a1-1) and potassium phthalimide (a2) were caused to react with each other to obtain 2,3-diamino-1,4-naphthoquinone (diaminonaphthoquinone (A)).

Specifically, 4.54 g (0.020 mol) of 2,3-dichloro-1,4-naphthoquinone, 7.40 g (0.040 mol) of potassium phthalimide, and 100 mL of acetonitrile were placed in a flask to prepare an acetonitrile solution. The acetonitrile solution was heated and refluxed under stirring at 80° C. for 5 hours. The reaction system after the reflux was left to stand to cool to room temperature (approximately 25° C.). Then, a resultant yellow solid (reaction intermediate product) was collected by filtration.

Then, 200 mL of 20% by mass aqueous hydrazine solution was added to the yellow solid, and the reaction system was stirred at room temperature (approximately 25° C.) for 30 minutes. The reaction system was heated and stirred for 1 hour at around 80° C. Filtration under heating was performed to collect a solid. The obtained solid was washed with water and then dried, whereby 2,3-diamino-1,4-naphthoquinone was obtained. The mass yield of 2,3-diamino-1,4-naphthoquinone was 2.80 g, and the percentage yield of 2,3-diamino-1,4-naphthoquinone relative to 2,3-dichloro-1,4-naphthoquinone was 74 mol %.

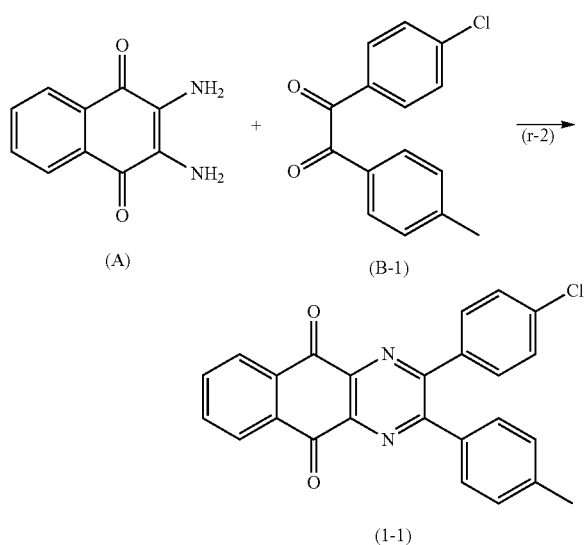

In the reaction (r-2), 2,3-diamino-1,4-naphthoquinone (diaminonaphthoquinone (A)) and a diketone derivative represented by chemical formula (B-1) (a diketone derivative (B-1)) were caused to react with each other to obtain a naphthoquinone derivative (1-1).

Specifically, 1.88 g (0.010 mol) of 2,3-diamino-1,4-naphthoquinone, 2.58 g (0.010 mol) of the diketone derivative (B-1), and 100 mL of ethanol were placed in a flask to prepare an ethanol solution. Then, 0.30 g (0.005 mol) of acetic acid was added to the ethanol solution. The reaction system was heated and refluxed under stirring at 80° C. for 4 hours. Ethanol was evaporated from the reaction system after the reflux to obtain a residue. The obtained residue was purified by silica gel column chromatography using chloroform as a developing solvent, whereby the naphthoquinone derivative (1-1) was obtained. The mass yield of the naphthoquinone derivative (1-1) was 2.46 g, and the percentage yield of the naphthoquinone derivative (1-1) relative to 2,3-diamino-1,4-naphthoquinone was 60 mol %.

[1-1-2. Production of Naphthoquinone Derivatives (1-2) to (1-5)]

The naphthoquinone derivatives (1-2) to (1-5) were produced by the same method as the method for producing the naphthoquinone derivative (1-1) in all aspects other than the following changes in the reaction (r-2). Note that the reaction (r-1) in production of the naphthoquinone derivatives (1-2) to (1-5) was the same as the reaction (r-1) in production of the naphthoquinone derivative (1-1). Also, raw materials used in production of the naphthoquinone derivatives (1-2) to (1-5) were each added in the same number of moles as that of a corresponding raw material used in production of the naphthoquinone derivative (1-1).

Table 1 shows 2,3-diamino-1,4-naphthoquinone (diaminonaphthoquinone (A)), diketone derivatives (B), and naphthoquinone derivatives (1) in the reaction (r-2). In the column under "Naphthoquinone derivative (1)" of Table 1, "1-1", "1-2", "1-3", "1-4", and "1-5" respectively represent the naphthoquinone derivatives (1-1), (1-2), (1-3), (1-4), and (1-5). Any of diketone derivatives (B-2) to (B-5) was used instead of the diketone derivative (B-1) in the reaction (r-2). As a result, any of the naphthoquinone derivatives (1-2) to (1-5) was obtained instead of the naphthoquinone derivative (1-1) through the reaction (r-2).

Table 1 shows the mass yields and the percentage yields of the naphthoquinone derivatives (1). Note that "A" in the column under "Diaminonaphthoquinone (A)" of Table 1 represents 2,3-diamino-1,4-naphthoquinone. Also, "B-1", "B-2", "B-3", "B-4", and "B-5" in the column under "Diketone derivative (B)" respectively represent the diketone derivatives (B-1), (B-2), (B-3), (B-4), and (B-5). The diketone derivatives (B-2), (B-3), (B-4), and (B-5) are respectively represented by chemical formulas (B-2), (B-3), (B-4), and (B-5) shown below.

TABLE 1

| | | | Reaction (r-2) | | | | |
|---|---|---|---|---|---|---|---|
| Diaminonaphthoquinone (A) | | | Diketone derivative (B) | | | Naphthoquinone derivative (1) | |
| | | | | | | Mass | Percentage |
| Type | Amount [g] | Amount [mol] | Type | Amount [g] | Amount [mol] | Type | yield [g] | yield [mol %] |
| A | 1.88 | 0.010 | B-1 | 2.58 | 0.010 | 1-1 | 2.46 | 60 |
| A | 1.88 | 0.010 | B-2 | 2.44 | 0.010 | 1-2 | 2.18 | 55 |
| A | 1.88 | 0.010 | B-3 | 2.42 | 0.010 | 1-3 | 2.36 | 60 |
| A | 1.88 | 0.010 | B-4 | 1.62 | 0.010 | 1-4 | 2.04 | 65 |
| A | 1.88 | 0.010 | B-5 | 2.17 | 0.010 | 1-5 | 2.21 | 60 |

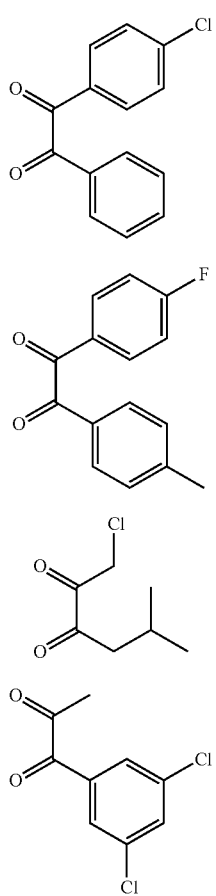

(B-2)

(B-3)

(B-4)

(B-5)

Next, $^1$H-NMR spectra of the produced naphthoquinone derivatives (1-1) to (1-5) were measured using a proton nuclear magnetic resonance spectrometer (product of JASCO Corporation, 270 MHz). CDCl$_3$ was used as a solvent. Tetramethylsilane (TMS) was used as an internal standard sample. The following describes the naphthoquinone derivative (1-4) as a representative example.

Figure 3:
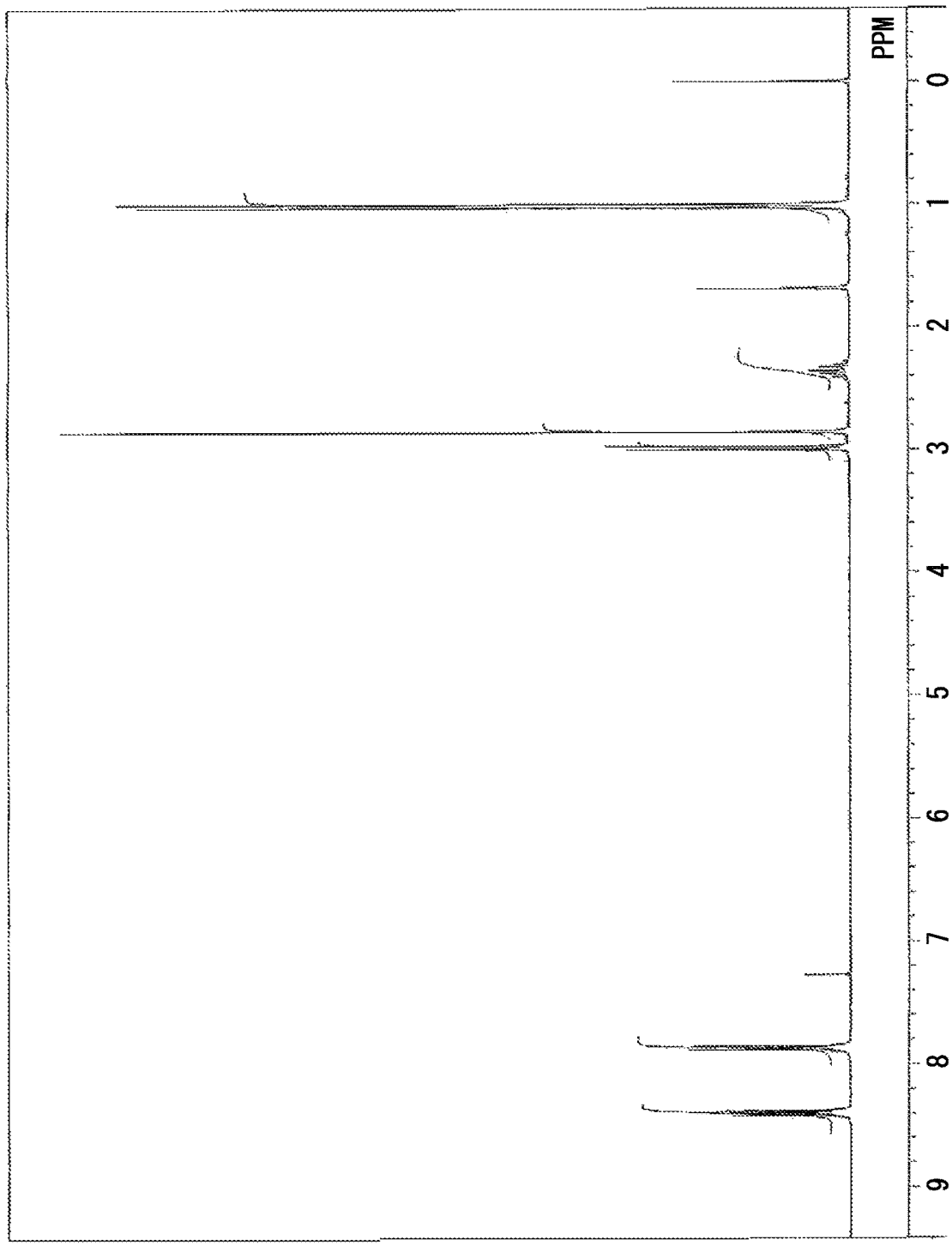
FIG. 3 is a $^1$H-NMR spectrum of a naphthoquinone derivative (1-4).

FIG. 3 shows the $^1$H-NMR spectrum of the naphthoquinone derivative (1-4). In FIG. 3, the vertical axis indicates intensity of signal (unit: arbitrary unit) and the horizontal axis indicates chemical shift (unit: ppm). The followings are chemical shift values of the naphthoquinone derivative (1-4).

Naphthoquinone derivative (1-4): $^1$H-NMR (270 MHz, CDCl$_3$) δ=8.36-8.43 (m, 2H), 7.83-7.90 (m, 2H), 3.00 (d, 2H), 2.86 (s, 2H), 2.36 (m, 1H), 1.02 (d, 6H).

Based on the $^1$H-NMR spectrum and the chemical shift values, it was confirmed that the naphthoquinone derivative (1-4) was obtained. Similarly, it was confirmed that the naphthoquinone derivatives (1-1) to (1-3) and (1-5) were obtained based on the respective $^1$H-NMR spectra and chemical shift values.

[1-1-3. Preparation of Compounds (E-1) to (E-3)]

The compounds (E-1) to (E-3) were prepared as electron transport materials.

[1-2. Hole Transport Material]

The compound (H-1) described in the first embodiment was prepared as the hole transport material.

[1-3. Charge Generating Material]

The compound (C-1) described in the first embodiment was prepared as the charge generating material. The compound (C-1) is a metal-free phthalocyanine (X-form metal-free phthalocyanine) represented by chemical formula (C-1). The compound (C-1) has the X-form crystal structure.

[1-4. Binder Resin]

The polycarbonate resins (R-1) and (R-2) described in the first embodiment were prepared as the binder resins.

<2. Production of Single-Layer Photosensitive Member>

Single-layer photosensitive members (A-1) to (A-10) and (B-1) to (B-6) were produced using the materials for forming the photosensitive layers.

[2-1. Production of Single-Layer Photosensitive Member (A-1)]

First, 3 parts by mass of the compound (C-1) as the charge generating material, 55 parts by mass of the compound (H-1) as the hole transport material, 30 parts by mass of the naphthoquinone derivative (1-1) as the electron transport material, 100 parts by mass of the polycarbonate resin (R-1) as the binder resin, and 600 parts by mass of tetrahydrofuran as a solvent were placed in a vessel. The vessel contents were mixed for 12 hours using a ball mill to disperse the materials in the solvent. Through the above, an application liquid for photosensitive layer formation was obtained. The application liquid for photosensitive layer formation was applied by dip coating onto a drum-shaped aluminum support as a conductive substrate. The applied application liquid for photosensitive layer formation was dried by blowing hot air at 120° C. for 80 minutes. Through the above, a photosensitive layer (single-layer photosensitive layer, film thickness: 30 μm) was formed on the conductive substrate. As a result, the single-layer photosensitive member (A-1) was obtained.

[2-2. Production of Single-Layer Photosensitive Members (A-2) to (A-10) and (B-1) to (B-6)]

The single-layer photosensitive members (A-2) to (A-10) and (B-1) to (B-6) were produced by the same method as the method for producing the single-layer photosensitive member (A-1) in all aspects other than the following changes. In production of each single-layer photosensitive member, a photosensitive layer having a film thickness of 30 μm was formed on a conductive substrate.

The naphthoquinone derivative (1-1) used as the electron transport material in production of the single-layer photosensitive member (A-1) was changed to any of electron transport materials shown in Table 2. The binder resin used in production of the single-layer photosensitive member (A-1) was changed to any of binder resins shown in Table 2. Table 2 shows compositions of the photosensitive members (A-1) to (A-10) and (B-1) to (B-6). In Table 2, "Resin", "CGM", "HTM", and "ETM" respectively represent binder resin, charge generating material, hole transport material, and electron transport material. In Table 2, "R-1" and "R-2" in the column under "Resin" respectively represent the polycarbonate resin (R-1) and the polycarbonate resin (R-2). Also, "x-$H_2$Pc" in the column under "CGM" represents the X-form metal-free phthalocyanine (compound (C-1)). "H-1" in the column under "HTM" represents the compound (H-1). Further, "1-1", "1-2", "1-3", "1-4", and "1-5" in the column under "ETM" respectively represent the naphthoquinone derivatives (1-1), (1-2), (1-3), (1-4), and (1-5). Also, "E-1", "E-2", and "E-3" in the column under "ETM" respectively represent the compounds (E-1), (E-2), and (E-3).

<3. Evaluation of Photosensitive Members>

[3-1. Evaluation of Electrical Characteristic (Sensitivity Characteristic) of Single-Layer Photosensitive Members]

An electrical characteristic (sensitivity characteristic) was evaluated with respect to each of the produced single-layer photosensitive members (A-1) to (A-10) and (B-1) to (B-6). The electrical characteristic was evaluated in an environment at a temperature of 23° C. and a humidity (relative humidity) of 50%.

First, a surface of each single-layer photosensitive member was positively charged using a drum sensitivity test device (product of Gen-Tech, Inc.). Charging was performed under the following conditions. That is, a rotational speed of the single-layer photosensitive member was set at 31 rpm. A surface potential of the single-layer photosensitive member right after the charging was set at +600 V. Then, monochromatic light (wavelength: 780 nm, half-width: 20 nm, optical energy: 1.5 μJ/cm$^2$) was obtained from white light emitted from a halogen lamp using a bandpass filter. The surface of the single-layer photosensitive member was irradiated with the obtained monochromatic light. A surface potential of the single-layer photosensitive member was measured when 0.5 seconds elapsed from termination of the irradiation. The measured surface potential was determined to be a post-irradiation electric potential ($V_L$, unit: V). The measured post-irradiation electric potential ($V_L$) of each single-layer photosensitive member is shown in Table 2. The smaller an absolute value of the post-irradiation electric potential ($V_L$) is, more excellent the sensitivity characteristic of the single-layer photosensitive member is.

[3-2. Evaluation of Electrical Characteristic (Triboelectric Chargeability) of Single-Layer Photosensitive Members]

Figure 4:
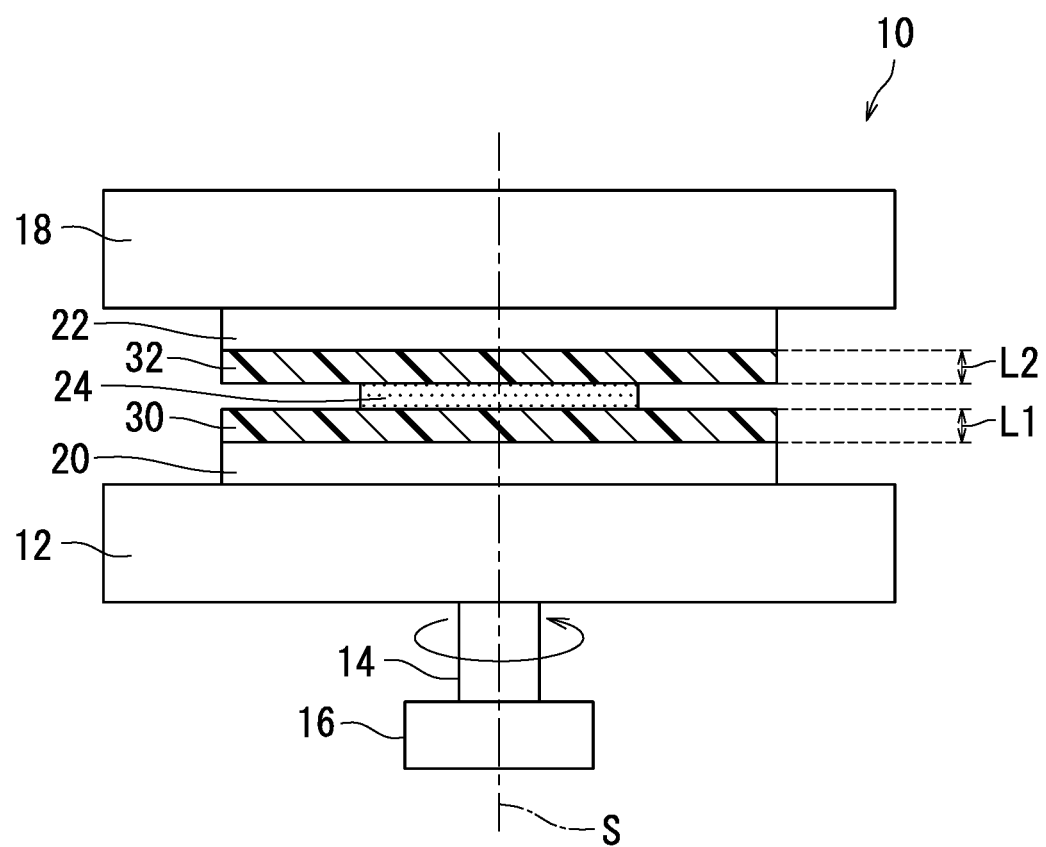
FIG. 4 is a diagram schematically illustrating a triboelectric charge measuring device.

An amount of charge (triboelectric charge) of calcium carbonate was measured by charging the calcium carbonate through friction with the photosensitive layer. Calcium carbonate is a main component of paper dust. The following describes with reference to FIG. 4 a method for measuring an amount of triboelectric charge of calcium carbonate by charging the calcium carbonate through friction with the photosensitive layer. FIG. 4 is a schematic illustration of a triboelectric charge measuring device. The amount of triboelectric charge of calcium carbonate was measured by the first through fourth steps described below. A jig 10 was used in the measurement of the amount of triboelectric charge of calcium carbonate.

As illustrated in FIG. 4, the jig 10 includes a first table 12, a rotary shaft 14, a rotary driving device 16 (for example, a motor), and a second table 18. The rotary driving device 16 causes the rotary shaft 14 to rotate. The rotary shaft 14 rotates about a rotation axis S of the rotary shaft 14. The first table 12 rotates together with the rotary shaft 14 about the rotation axis S. The second table 18 is secured and does not rotate.

(First Step)

Two photosensitive layers were prepared in the first step. In the following description, one of the photosensitive layers will be referred to as a first photosensitive layer 30 and the other of the photosensitive layers will be referred to as a second photosensitive layer 32. The application liquid for single-layer photosensitive layer formation prepared in production of any of the above-described single-layer photosensitive members (A-1) to (A-10) and (B-1) to (B-6) was applied onto an overhead projector sheet (hereinafter may be referred to as an OHP sheet) wound around an aluminum pipe (diameter: 78 mm). The applied application liquid was dried at 120° C. for 80 minutes. Through the above, a sheet for triboelectric chargeability evaluation was obtained. The obtained sheet included a photosensitive layer having a film thickness of 30 μm formed thereon. Thus, a first sheet and a second sheet were obtained. The first sheet included a first OHP sheet 20 and the first photosensitive layer 30 (film thickness L1: 30 μm). The second sheet included a second OHP sheet 22 and the second photosensitive layer 32 (film thickness L2: 30 μm). The first OHP sheet 20 and the second OHP sheet 22 each had a length of 5 cm and a width of 5 cm.

(Second Step)

In the second step, 0.007 g of calcium carbonate was placed on the first photosensitive layer 30. Then, the second photosensitive layer 32 was placed on the thus formed calcium carbonate layer 24. Specifically, the second step was carried out as follows.

First, the first OHP sheet 20 was bonded to the first table 12 using double sided tape to fix the first sheet on the first table 12. Also, the second OHP sheet 22 was bonded to the second table 18 using double sided tape to fix the second sheet on the second table 18. Further, 0.007 g of calcium carbonate was placed on the first photosensitive layer 30 included in the first sheet to form the calcium carbonate layer 24 having a uniform film thickness. The amount of the calcium carbonate was determined so that calcium carbonate could be sufficiently and evenly charged through sufficient and even friction thereof with the first photosensitive layer 30 and the second photosensitive layer 32 in 60-second rotation of the rotary shaft 14 in the third step. The calcium carbonate layer 24 was formed around the rotation axis S to be located further inward than the periphery of the first photosensitive layer 30 so that the calcium carbonate would not drop out from between the first photosensitive layer 30 and the second photosensitive layer 32 when the rotary driving device 16 was driven in the third step. Then, the second photosensitive layer 32 was placed on the calcium carbonate layer 24 by bringing the second photosensitive layer 32 into contact with the calcium carbonate layer 24 such that the first photosensitive layer 30 and the second photosensitive layer 32 faced each other with the calcium carbonate layer 24 interposed therebetween. Through the above, the first table 12, the first OHP sheet 20, the first photosensitive layer 30, the calcium carbonate layer 24, the second photosensitive layer 32, the second OHP sheet 22, and the second table 18 were layered in this order from the bottom. The first table 12, the first OHP sheet 20, the first photosensitive layer 30, the calcium carbonate layer 24, the second photosensitive layer 32, the second OHP sheet 22, and the second table 18 were arranged such that respective centers thereof coincided with the rotation axis S.

(Third Step)

In the third step, the first photosensitive layer 30 was rotated at a rotational speed of 60 rpm for 60 seconds while the second photosensitive layer 32 was kept stationary in an environment at a temperature of 23° C. and a relative humidity of 50%. Specifically, the rotary driving device 16 was driven to rotate the rotary shaft 14, the first table 12, the first OHP sheet 20, and the first photosensitive layer 30 about the rotation axis S at a rotational speed of 60 rpm for 60 seconds. As a result, the calcium carbonate was charged through friction with each of the first photosensitive layer 30 and the second photosensitive layer 32.

(Fourth Step)

In the fourth step, the calcium carbonate charged in the third step was collected from the jig 10 and sucked using a charge measuring device (compact draw-off charge measurement system, "MODEL 212HS" manufactured by TREK, INC.). A total amount of electricity Q (unit: μC) and a mass M (unit: g) of the sucked calcium carbonate were measured using the charge measuring device. An amount of triboelectric charge (unit: μC/g) of the calcium carbonate was calculated by the following equation "triboelectric charge=Q/M".

The measured amount of triboelectric charge of the calcium carbonate is shown in Table 2. Note that a larger positive value of the amount of triboelectric charge of the calcium carbonate indicates a stronger tendency of the calcium carbonate to be positively charged relative to the first photosensitive layer 30 and the second photosensitive layer 32. Also, a larger positive value of the amount of triboelectric charge of calcium carbonate indicates a stronger tendency of calcium carbonate to be negatively charged relative to the first photosensitive layer 30 and the second photosensitive layer 32.

[3-3. Evaluation of Image Characteristic (Measurement of Number of White Spots)]

An image characteristic was evaluated with respect to each of the produced single-layer photosensitive members (A-1) to (A-10) and (B-1) to (B-6). The image characteristic was evaluated in an environment at a temperature of 32.5° C. and a relative humidity of 80%. An image forming apparatus ("MONOCHROME PRINTER FS-1300D" manufactured by KYOCERA Document Solutions Inc.) was used as an evaluation apparatus. The image forming apparatus adopts the contact development process, the direct transfer process, and the blade cleaner-less process. The image forming apparatus includes a scorotron charger as a charger. A recording medium used was "KYOCERA Document Solutions brand paper VM-A4" (A4 size) sold by KYOCERA Document Solutions Inc. A one-component developer (test sample) was used in the evaluation performed using the evaluation apparatus.

An image I (image at a printing rate of 1%) was continuously printed on 20,000 recording mediums under a condition of a rotational speed of the single-layer photosensitive member of 168 mm/second using the evaluation apparatus. Subsequently, an image II (black solid image, length: 297 mm, width: 210 mm, A4 size) was printed on a single recording medium. The recording medium with the image II formed thereon was observed with unaided eyes to determine presence or absence of an image defect in the formed image. The number of white spots that the black solid image had was counted as image defects. The black solid image tends to have white spots when paper dust is attached to the photosensitive member. Table 2 shows the number of white spots that the black solid image had. A smaller number of white spots indicates that occurrence of image defects (occurrence of the white spot phenomenon) due to attachment of paper dust was inhibited more effectively.

TABLE 2

|  | Photosensitive member No. | Photosensitive layer | | | | Electrical characteristics | | Image characteristic |
|---|---|---|---|---|---|---|---|---|
|  |  | Resin | CGM | HTM | ETM | Post-irradiation potential $V_L$ (V) | Triboelectric charge (μC/g) | Number of white spots |
| Example 1 | A-1 | R-1 | x-$H_2$Pc | H-1 | 1-1 | +149 | +9.2 | 34 |
| Example 2 | A-2 | R-2 | x-$H_2$Pc | H-1 | 1-1 | +144 | +9.0 | 32 |
| Example 3 | A-3 | R-1 | x-$H_2$Pc | H-1 | 1-2 | +151 | +9.3 | 34 |
| Example 4 | A-4 | R-2 | x-$H_2$Pc | H-1 | 1-2 | +152 | +9.2 | 33 |
| Example 5 | A-5 | R-1 | x-$H_2$Pc | H-1 | 1-3 | +150 | +9.1 | 31 |
| Example 6 | A-6 | R-2 | x-$H_2$Pc | H-1 | 1-3 | +150 | +9.3 | 32 |
| Example 7 | A-7 | R-1 | x-$H_2$Pc | H-1 | 1-4 | +155 | +9.1 | 33 |
| Example 8 | A-8 | R-2 | x-$H_2$Pc | H-1 | 1-4 | +153 | +9.1 | 30 |
| Example 9 | A-9 | R-1 | x-$H_2$Pc | H-1 | 1-5 | +155 | +9.2 | 28 |
| Example 10 | A-10 | R-2 | x-$H_2$Pc | H-1 | 1-5 | +156 | +9.4 | 26 |
| Comparative Example 1 | B-1 | R-1 | x-$H_2$Pc | H-1 | E-1 | +152 | +5.3 | 100 |
| Comparative Example 2 | B-2 | R-2 | x-$H_2$Pc | H-1 | E-1 | +148 | +5.6 | 97 |
| Comparative Example 3 | B-3 | R-1 | x-$H_2$Pc | H-1 | E-2 | +129 | +6.2 | 55 |
| Comparative Example 4 | B-4 | R-2 | x-$H_2$Pc | H-1 | E-2 | +131 | +6.0 | 57 |
| Comparative Example 5 | B-5 | R-1 | x-$H_2$Pc | H-1 | E-3 | +158 | +6.9 | 46 |
| Comparative Example 6 | B-6 | R-2 | x-$H_2$Pc | H-1 | E-3 | +162 | +6.7 | 44 |

As shown in Table 2, in each of the photosensitive members (A-1) to (A-10), the photosensitive layer includes a charge generating material, a hole transport material, and any one of the naphthoquinone derivatives (1-1) to (1-5) as an electron transport material. The naphthoquinone derivatives (1-1) to (1-5) are each the naphthoquinone derivative (1). With respect to each of the photosensitive members (A-1) to (A-10), the amount of triboelectric charge of calcium carbonate is at least +9.0 µC/g and no greater than +9.4 µC/g. Also, with respect to each of the photosensitive members (A-1) to (A-10), the number of white spots is at least 26 and no greater than 34.

As shown in Table 2, in each of the photosensitive members (B-1) to (B-6), the photosensitive layer includes a charge generating material, a hole transport material, and any one of the compounds (E-1) to (E-3) as an electron transport material. Each of the compounds (E-1) to (E-3) is not the naphthoquinone derivative (1). With respect to each of the photosensitive members (B-1) to (B-6), the amount of triboelectric charge of calcium carbonate is at least +5.3 µC/g and no greater than +6.9 µC/g, that is, smaller than +7 µC/g. Also, with respect to each of the photosensitive members (B-1) to (B-6), the number of white spots is at least 44 and no greater than 100.

It is evident that the photosensitive members (A-1) to (A-10) each including the photosensitive layer containing the naphthoquinone derivative (1) can inhibit occurrence of the white spot phenomenon more effectively than the photosensitive members (B-1) to (B-6) including the photosensitive layers each containing a corresponding one of the compounds (E-1) to (E-3), which were not the naphthoquinone derivative (1). Also, it is evident that an image forming apparatus including any of the photosensitive members (A-1) to (A-10) can inhibit occurrence of the white spot phenomenon more effectively than an image forming apparatus including any of the photosensitive members (B-1) to (B-6).

As shown in Table 2, in each of the photosensitive members (A-9) and (A-10) among the photosensitive members (A-1) to (A-10), the photosensitive layer contains the naphthoquinone derivative (1-5) as an electron transport material. The naphthoquinone derivative (1-5) is a naphthoquinone derivative (1) that has an alkyl group and a phenyl group substituted with a plurality of halogen atoms. With respect to the photosensitive member (A-9), the number of white spots is 28. With respect to the photosensitive member (A-10), the number of white spots is 26. From these results, it is evident that the photosensitive members (A-9) and (A-10) each including the photosensitive layer containing as the electron transport material the naphthoquinone derivative (1), which has an alkyl group and a phenyl group substituted with halogen atoms, has a particularly strong effect of inhibiting occurrence of the white spot phenomenon.

INDUSTRIAL APPLICABILITY

The photosensitive member and the process cartridge according to the present invention can be used in an image forming apparatus. The image forming apparatus according to the present invention can be used as a copier or a printer.

The invention claimed is:

1. An electrophotographic photosensitive member comprising a conductive substrate and a photosensitive layer, wherein
the photosensitive layer is a single-layer photosensitive layer containing at least a charge generating material, an electron transport material, a hole transport material, and a binder resin,
the electron transport material includes a naphthoquinone derivative represented by a general formula (1),
an amount of triboelectric charge of calcium carbonate as measured by charging the calcium carbonate through friction with the photosensitive layer is at least +7 µC/g, in the measurement of the amount of triboelectric charge of the calcium carbonate, (i) two of the photosensitive layers are prepared, one of the two photosensitive layers being a first photosensitive layer, another of the two photosensitive layers being a second photosensitive layer, the first photosensitive layer having a film thickness of 30 µm and being formed on a first overhead projector sheet, the second photosensitive layer having a film thickness of 30 µm and being formed on a second overhead projector sheet, the first overhead projector sheet and the second overhead projector sheet each having a length of 5 cm and a width of 5 cm,
(ii) 0.007 g of the calcium carbonate is placed on the first photosensitive layer to form a calcium carbonate layer formed from the calcium carbonate, and the second photosensitive layer is placed on the calcium carbonate layer,
(iii) the first photosensitive layer is rotated at a rotational speed of 60 rpm for 60 seconds while the second photosensitive layer is kept stationary in an environment at a temperature of 23° C. and a relative humidity of 50% to charge the calcium carbonate through friction between the calcium carbonate and each of the first photosensitive layer and the second photosensitive layer, and
(iv) the charged calcium carbonate is sucked using a charge measuring device, and a total amount of electricity Q and a mass M of the sucked calcium carbonate are measured using the charge measuring device to calculate the amount of triboelectric charge of the calcium carbonate by an equation "amount of triboelectric charge=Q/M",

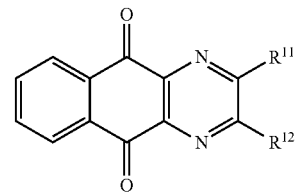

(1)

where in the general formula (1),
$R^{11}$ and $R^{12}$ each represent, independently of each other, a chemical group selected from the group consisting of: an alkyl group having a carbon number of at least 1 and no greater than 8; an aryl group having a carbon number of at least 6 and no greater than 14 and optionally having a substituent; an aralkyl group having a carbon number of at least 7 and no greater than 20 and optionally having a substituent; and a cycloalkyl group having a carbon number of at least 3 and no greater than 10 and optionally having a substituent, and
at least one of the chemical groups respectively represented by $R^{11}$ and $R^{12}$ is substituted with one or more halogen atoms.

2. The electrophotographic photosensitive member according to claim 1, wherein
in the general formula (1),
the aryl group having a carbon number of at least 6 and no greater than 14 has an alkyl group having a carbon number of at least 1 and no greater than 6 as the substituent,
the aralkyl group having a carbon number of at least 7 and no greater than 20 has an alkyl group having a carbon number of at least 1 and no greater than 6 as the substituent, and the cycloalkyl group having a carbon number of at least 3 and no greater than 10 has an alkyl group having a carbon number of at least 1 and no greater than 6 as the substituent.

3. The electrophotographic photosensitive member according to claim 1, wherein in the general formula (1), a total number of halogen atoms included in the chemical groups respectively represented by $R^{11}$ and $R^{12}$ is at least 1 and no greater than 3.

4. The electrophotographic photosensitive member according to claim 1, wherein in the general formula (1), $R^{11}$ and $R^{12}$ differ from each other.

5. The electrophotographic photosensitive member according to claim 1, wherein in the general formula (1), either one of $R^{11}$ and $R^{12}$ represents an alkyl group having a carbon number of at least 1 and no greater than 3 and substituted with one or more halogen atoms, or a phenyl group substituted with one or more halogen atoms, the other of $R^{11}$ and $R^{12}$ represents: a phenyl group optionally having an alkyl group having a carbon number of at least 1 and no greater than 3; or an alkyl group having a carbon number of at least 1 and no greater than 4, and the one or more halogen atoms are each a chlorine atom or a fluorine atom.

6. The electrophotographic photosensitive member according to claim 5, wherein in the general formula (1), either one of $R^{11}$ and $R^{12}$ represents a phenyl group and substituted with one or more halogen atoms, and the other of $R^{11}$ and $R^{12}$ represents an alkyl group having a carbon number of at least 1 and no greater than 4.

7. The electrophotographic photosensitive member according to claim 1, wherein the naphthoquinone derivative is represented by a chemical formula (1-1), (1-2), (1-3), (1-4), or (1-5)

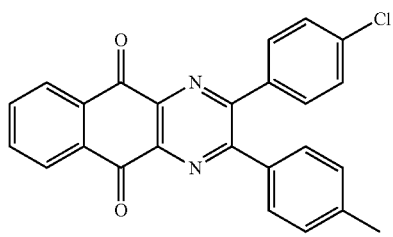

(1-1)

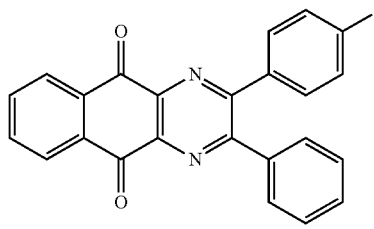

(1-2)

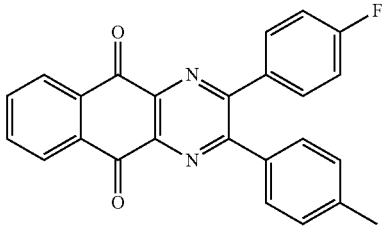

(1-3)

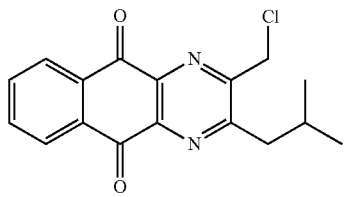

(1-4)

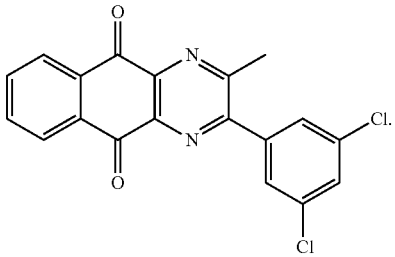

(1-5)

8. The electrophotographic photosensitive member according to claim 1, wherein the hole transport material includes a compound represented by a general formula (2),

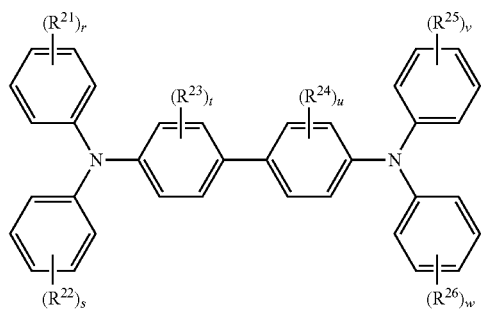

(2)

where in the general formula (2), $R^{21}$, $R^{22}$, $R^{23}$, $R^{24}$, $R^{25}$, and $R^{26}$ each represent, independently of one another, an alkyl group having a carbon number of at least 1 and no greater than 6 or an alkoxy group having a carbon number of at least 1 and no greater than 6, r, s, v, and w each represent, independently of one another, an integer of at least 0 and no greater than 5, and t and u each represent, independently of each other, an integer of at least 0 and no greater than 4.

9. The electrophotographic photosensitive member according to claim 1, wherein the binder resin includes a polycarbonate resin represented by a general formula (3),

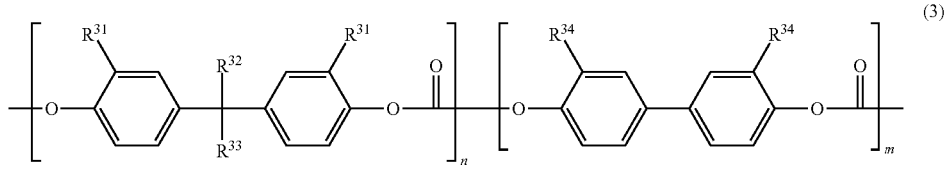

(3)

where in the general formula (3), $R^{31}$, $R^{32}$, $R^{33}$, and $R^{34}$ each represent, independently of one another, a hydrogen atom or an alkyl group having a carbon number of at least 1 and no greater than 6, $R^{32}$ and $R^{33}$ may be bonded to each other to form a cycloalkylidene group having a carbon number of at least 3 and no greater than 10, n and m each represent an integer of at least 0, n+m=100, and n represents an integer of at least 60 and no greater than 100.

10. A process cartridge comprising the electrophotographic photosensitive member according to claim 1; and at least one device selected from the group consisting of a charger, a light exposure device, a developing device, and a transfer device.

11. An image forming apparatus comprising:
an image bearing member;
a charger configured to positively charge a surface of the image bearing member;
a light exposure device configured to irradiate the charged surface of the image bearing member with light to form an electrostatic latent image on the surface of the image bearing member;
a developing device configured to develop the electrostatic latent image into a toner image; and
a transfer device configured to transfer the toner image from the surface of the image bearing member to a recording medium while in contact with the surface of the image bearing member, wherein
the image bearing member is the electrophotographic photosensitive member according to claim 1.

12. The image forming apparatus according to claim 11, wherein
the charger is a charging roller.

13. The image forming apparatus according to claim 11, wherein
the developing device is configured to develop the electrostatic latent image into the toner image while in contact with the surface of the image bearing member.

14. The image forming apparatus according to claim 11, wherein
the developing device is configured to clean the surface of the image bearing member.

* * * * *